United States Patent [19]
Margolis et al.

[11] Patent Number: 5,262,409
[45] Date of Patent: Nov. 16, 1993

[54] BINARY TUMOR THERAPY

[75] Inventors: Robert L. Margolis; Paul R. Andreasson, both of Seattle, Wash.

[73] Assignee: Fred Hutchinson Cancer Research Center, Seattle, Wash.

[21] Appl. No.: 776,065

[22] Filed: Oct. 11, 1991

[51] Int. Cl.$^5$ .................... A01N 43/00; A01N 43/90; A61K 31/33; A61K 31/52

[52] U.S. Cl. .................... 514/183; 514/261; 514/283; 514/411; 514/443; 514/444; 514/449; 514/463; 514/468

[58] Field of Search ............... 514/183, 261, 283, 411, 514/443, 444, 449, 463, 468

[56] References Cited

OTHER PUBLICATIONS

Bailel, E., et al. 1989 p34$^{cdc2}$ is located in both nucleus and cytoplasm; part is centrosomally associated at G2/M and enters vesicles at anaphase. *EMBO J.*, 8:3985–3995.

Belenguer, P., et al. 1990. Mitosis-specific phosphorylation of nucleolin by p34$^{cdc2}$ kinase. *Mol. Cell. Biol.* 10:3607–3618.

Bialojan, C. & Takai, A. (1988), Inhibitory effect of a marine-sponge toxin, okadaic acid, on protein phosphatases, *Biochemical Journal*, 256:283–290.

Blow, J. J. & Nurse, P. (1990), A cdc2-like protein is involved in the initiation of DNA replication in Xenopus egg extracts, *Cell*, 62:855–862.

Bravo, R. & MacDonald-Bravo, H. (1985), *EMBO J.*, 4:655–661.

Browne, C. L., et al. 1987. Effect of inhibition of the catalytic activity of cyclic AMP-dependent protein kinase on mitosis in PtK cells. *Cell Motil. and the Cytoskel.* 7:248–257.

Caras, I. W., et al. 1982. Mechanism of 2-Aminopurine mutagenesis in mouse T-lymphosarcoma cells. *Molec. Cell Biol.* 2:1096–1103.

Chackalaparampil, I., and Shalloway, D. 1988. Altered phosphorylation and activation of PP60$^{c-src}$ during fibroblast mitosis. *Cell* 52:801–810.

Charron, M. & Hancock, R. (1990), *Biochemistry*, 29:9531–9537.

Chen, G. L., et al. (1984), Nonintercalative antitumor drugs interfere with the breakage—reunion reaction of mammalian topoisomerase II, *J. Biological Chem.*, 259:13560–13566.

Chou, Y. H., et al. 1990. Intermediate filament reorganization is mediated by p34$^{cdc2}$ phosphorylation of vimentin. *Cell* 62:1063–1071.

Dasso, M. and Newport, J. W. (1990), Completion of DNA replication is monitored by a feedback system (List continued on next page.)

*Primary Examiner*—Nathan M. Nutter
*Attorney, Agent, or Firm*—Christensen, O'Connor, Johnson & Kindness

[57] ABSTRACT

Method for killing a cycling cell, by contacting the cell with a first agent that blocks progression of the cell cycle in the cell, and thereafter contacting the cell with a second agent that overrides the cell cycle block such that the cell proceeds past mitosis and cell death results within an additional cell cycle due to aberrant DNA replication or chromosome segregation. The first agent blocks the progression of the $G_1$, S, $G_2$, or mitosis stage of the cell cycle. The second agent is preferably 2-aminopurine (2-AP) or 6-dimethylaminopurine (6-DMAP). The duration of contact with the first agent is advantageously limited to a first time period sufficient to block the progression of the cell cycle, and the duration of contact with the second agent is limited to a second time period sufficient to override the cell cycle block. Also, a method of screening for a binary tumor therapy agent, by contacting a cycling mammalian cell with a first agent that blocks progression of the cell cycle, preferably mitosis, in the cell; thereafter contacting the cell with a candidate second agent; and determining that the candidate second agent is a binary tumor therapy agent if the candidate second agent overrides the cell cycle block such that the cell proceeds past mitosis and cell death results within an additional cell cycle due to aberrant DNA replication or chromosome segregation.

3 Claims, 16 Drawing Sheets

OTHER PUBLICATIONS that controls the initiation of mitosis in in vitro studies in Xenopus, *Cell,* 61:811–823.

Davis, F. M., et al. 1983. Monoclonal antibodies to mitotic cells. *Proc. Natl. Acad. Sci. USA* 80:2926–2930.

Docher, G. B., and Bennett, D. 1974. Abnormal microtubular systems in mouse spermatids associated with a mutant gene at the T–locus. *J. Embryol. and Exp. Morphol.* 32:749–762.

Downes, C. S., et al. 1990. Caffeine overcomes a restriction point associated with DNA replication, but does not accelerate mitosis, *J. Cell Biol.* 110:1855–1859.

Draetta, G. (1990), Cell cycle control in eukaryotes: molecular mechanisms of cdc2 activation, *Trends in Biochem. Sci.,* 15:378–383.

Dunphy, W. G., and Newport, J. W. 1988. Mitosis-inducing factors are present in a latent form during interphase in the *Xenopus* embryo. *J. Cell Biol.* 106:2047–2056.

D'Urso, G., et al. (1990), Cell cycle control of DNA regulation by a homologue from human cells of the $p34^{cdc2}$ protein kinase, *Science,* 250:786–791.

Earnshaw, W. C., et al. (1985), Topoisomerase is a structural component of mitotic chromosome scaffolds, *J. Cell Biology,* 100:1706–1715.

Fang, F. & Newport, J. W. (1991), Evidence that the G1–S and G2–M transitions are controlled by different cdc2 proteins in higher eukaryotes, *Cell,* 66:731–742.

Farrell, P. J., et al. (1977), Phosphorylation of initiation factor eIF-2 and the control of protein synthesis, *Cell,* 11:187–200.

Featherstone, C. & Russell, P. (1991), Fission yeast p107wee1 mitotic inhibitor is a tyrosine/serine kinase, *Nature,* 349:808–811.

Gotoh, Y., et al. 1991. In vitro effects on microtubule dynamics of purified *Xenopus* M phase-activated MAP kinase. *Nature* 349:251–254.

Gould, K. L. & Nurse, P. (1989), Tyrosine phosphorylation of the fission yeast cdc2+protein kinase regulates entry into mitosis, *Nature,* 342:39–45.

Guilly, M. N., et al. (1987), Autoantibodies to nuclear lamin B in a patient with thrombopenia, *Eur. J. Cell,* 43:266–272.

Guilly, M. N., et al. 1987b. A human T lymphoblastic cell line lacks lamins A and C. *EMBO J.* 6:3795–3799.

Hartwell, L. H. & Weinert, T. A. (1989), Checkpoints: controls that ensure the order of cell cycle events, *Science,* 246:629–634.

Hayden, J. H., et al. 1990. Kinetochores capture astral microtubules during chromosome attachment to the mitotic spindle: direct visualization in live newt lung cells, *J. Cell Biol.* 111:1039–1045.

Hoyt, M. A., Totis, L. & Roberts, B. T. (1991): *Cell* 66:507–517.

Ikegami, S., et al. (1978), Aphidicolin prevents mitotic cell division by interfering with the activity of DNA polymerase a, *Nature,* 275:458–460.

Igarashi, M., et al. (1991), Wee1$^{30}$–like gene in human cells, *Nature,* 353:80–83.

Johnson, et al., 1982. Fading of immunofluorescence during microscopy: a study of the phenomenon and its remedy. *J. Immunol. Methods* 55:231–242.

Kipreos, E. T., and Wang, J. Y. J. 1990. Differential phosphorylation of c-abl in cell cycle determined by cdc2 kinase and phosphatase activity. *Science* 248:217–220.

Lalande, M. (1990), A reversible arrest point in the late G1 phase of the mammalian cell cycle, *Experimental Cell Research,* 186:332–339.

Langan, T. A., et al. 1989. Mammalian growth-associated H1 histone kinase: a homolog of cdc2+/cdc28 protein kinases controlling mitotic entry in yeast and frog cells. *Mol. and Cell. Biol.* 9:3860–3868.

Lau, C. C. & Pardee, A. B. (1982), Mechanism by which caffeine potentiates lethality of nitrogen mustard, *Proc. Natl. Acad. Sci. U.S.A.,* 79:2942–2946.

Li, R. & Murray, A. W. (1991). *Cell* 66:519–531.

Liu, J., et al. 1990. Cell cycle-mediated structural and functional alteration of $p85^{gag-mos}$ protein kinase activity. *Oncogene* 5:171–178.

Lungren, K., et al. (1991), Mik1 and wee1 cooperate in the inhibitory tyrosine phosphorylation of cdc2, *Cell,* 64:1111–1122.

Mahadevan, L. C., et al. (1990), 2-aminopurine abolishes EGF-and TPA- stimulated pp33 phosphorylation and c-fos induction without affecting the activation of protein kinase C, *Oncogene,* 5:327–335.

Matsumoto, T. & Beach, D. (1991), Premature initiation of mitosis in yeast lacking RCC1 or an interacting GTPase, *Cell* 66:347–360.

(List continued on next page.)

OTHER PUBLICATIONS

McIntosh, J. R., and Porter, K. R. 1967. Microtubules in the spermatid of the domestic fowl. *J. Cell. Biol.* 35:153–173.

Minshull, J., et al. (1989), The role of cyclin synthesis, modification and destruction in the control of cell division, *J. Cell Science,* Suppl. 12:77–97.

Misra, N. C. & Roberts, D. (1975), Inhibition by 4'-demethyl-epidophyllotoxin 9-(4,6-O-2-thenyl-dene-b-D-glycopyranoside) of human lymphoblast cultures in G2 phase of the cell cycle, *Cancer Research,* 35:99–105.

Mitchison, T. J., and Kirschner, M. W. 1984. Dynamic instability of microtubule growth. *Nature* 312:237–242.

Mitchison, T. J., and Kirschner, M. W. 1985. Properties of the kinetochore in vitro. II. Microtubule capture and ATP-dependent translocation. *J. Cell Biol.* 101:766–777.

Moore, E. C. (1969). *Cancer Research* 29:291–295.

Morgan, D. O., et al. 1989. Mitosis-specific phosphorylation of p $60^{c\text{-}src}$ by $p34^{cdc2}$-associated protein kinase. *Cell* 57:775–786.

Mulner-Lorillon, O., et al. 1990. M-phase specific cdc2 protein kinase phosphorylates the beta subunit of casein kinase II and increases casein kinase II activity. *Eur. J. Biochem.* 193:529–534.

Murphy, P. 1976. The Neutrophil. Plenum Publishing Co., New York. 127 pp.

Murray, A. W., and Kirscher, M. W. (1989), Dominoes and clocks: the union of two views of the cell cycle, *Science,* 246:614–621.

Musk, S. R. R., et al. (1988), Caffeine induces uncoordinated expression of cell cycle functions after ultraviolet irradiation, *J. Cell Science,* 90:591–599.

Neant, I., and Guerrier, P. 1988. Meiosis reinitiation in the mollusc *Patella vialgata.* Regulation of MPF, CSF and chromosome condensation activity by intracellular pH, protein synthesis and phosphorylation. *Development* 102:505–516.

Newport, J., and Spann, T., 1987. Disassembly of the nucleus in mitotic extracts: membrane vesicularization, lamin disassembly, and chromosome condensation are independent processes. *Cell,* 48:219–230.

Nishimoto, T., et al. (1978), Premature chromosome condensation in a ts DNA-Mutant of BHK Cells, *Cell,* 15:475–483.

Nurse, P. (1990), Universal control mechanism regulating onset of M-phase, *Nature,* 344:503–508.

O'Dwyer, P. J., et al. (1984), Teniposide: a review of 12 years of experience, *Cancer Treatment Reports,* 12:1455–1466.

Ohtsubo, M. et al. (1987), Isolation and characterization of the active cDNA of the human cell cycle gene (RCC1) involved in the regulation of onset of chromosome condensation, *Genes and Development,* 1:585–593.

Osmani, S. A., et al. (1988), Spindle formation and condensation in cells blocked at interphase by mutation of a negative cell cycle control gene, *Cell,* 52:241–251.

Paschal, B. M., et al. 1987 MAPIC is a microtubule-activated ATPase which translocates microtubules *in vitro* and has dynein-like properties *J. Cell Biol.* 105:1273–1282.

Pelech, S. L., et al. 1988. Activation of myelin basic protein kinases during echinoderm oocyte maturation and egg fertilization *Dev. Biol.* 130:28–36.

Peter, M., et al. 1990a. Identification of major nucleolar proteins as candidate mitotic substrates of cdc2 kinase. *Cell,* 60:791–801.

Peter, M., et al. 1990b. *In vitro* disassembly of the nuclear lamina and M-phase-specific phosphorylation of lamins by cdc2 kinase. *Cell,* 61:591–602.

Pfarr, C. M., et al. 1990. Cytoplasmic dynein is localized to kinetochores during mitosis. *Nature,* 345:263–265.

Reed, S. I. (1991), G1-specific cyclins: in search of an S-phase promoting factor, *Trends in Genetics,* 7:95–99.

Riabowol, K., et al. 1989. The cdc2 kinase is a nuclear protein that is essential for mitosis in mammalian cells. *Cell,* 57:393–401.

Rieder, C. L. & Alexander, S. P. (1990), Kinetochores are transported poleward along a single astral microtubule during chromosome attachment to the spindle in newt lung cells, *J. Cell Biology,* 110:81–95.

Rime, H., et al. 1989. 6-dimethylaminopurine (6-D-MAP), a reversible inhibitor of the transition to metaphase during the first cell division of the mouse oocyte. *Dev. Biol.,* 133:169–179.

Rober, R.-A., et al. 1990. Cells of the cellular immune and hematopoietic system of the mouse lack lamins (List continued on next page.)

OTHER PUBLICATIONS

A/C: distinction versus other cells. *J. Cell Sci.*, 95:587–598.

Roberge, M., et al. (1990), The topoisomerase II inhibitor VM-26 induces marked changes in histone H1 kinase activity, histones H1 and H3 phosphorylation, and chromosome condensation in G2 phase and mitotic BHK cells, *J. Cell Biology*, 111:1753–1762.

Rowinsky, E. K., et al. (1990), Taxol: a novel investigational antimicrotubule agent, *J. Natl. Cancer Instit.*, 82:1247–1259.

Sawin, K. E., and Mitchison, T. J. 1991. Mitotic spindle assembly by two different paths in vitro *J. Cell Biol.*, 112:925–940.

Schaff, D. A., Jarrett, R. A., Dloughy, S. R., Ponniah, S., Stockelman, M., Stambrook, P. J. and Tischfield, J. A. 1990. Mouse transgenes in human cells detect specific base substitutions. *Proc. Natl. Acad. Sci.* 87:8675–8679.

Schiff, P. B. & Horwitz, S. B. (1980). *Proc. Natl. Acad. Sci. U.S.A.*, 77, 1561–1565.

Schlegel, R. & Pardee, A. B. (1986), Caffeine-induced uncoupling of mitosis from the completion of DNA replication in mammalian cells, *Science*, 232:1264–1266.

Schlegel, R., et al. (1990), Premature mitosis induced in mammalian cells by the protein kinase inhibitors 2-aminopurine and 6-dimethylaminopurine, *Cell Growth and Differentiation*, 1:171–178.

Shenoy, S. et al. 1989. Purified maturation promoting factor phosphorylates pp60$^{c-src}$ at the sites phosphorylated during fibroblast mitosis. *Cell*, 57:763–774.

Speit, G., et al. 1990. Genetic effects of 2-aminopurine in mammalian cells. *Mutagenesis*, 5:185–190.

Steinmann, K. E., et al. (1991), *Proc. Natl. Acad. Sci. U.S.A.*, 88:6843–6847.

Steuer, E. R., et al. (1990), Localization of cytoplasmic dynein to mitotic spindles and kinetochores. *Nature*, 345:266–269.

Takasaki, Y., et al. (1981), *J. Experimental Medicine*, 154:1899–1909.

Tate E. H., et al. (1983) *Cytometry*, 4:211–215.

Tobey, R. A. 1973. Production and characterization of mammalian cells reversibly arrested in $G_1$ by growth in isoleucine-deficient medium. *Meth. Cell. Biol.*, 6:67–112.

Vandre, D. D., et al. 1984. Phosphoproteins are components of mitotic microtubule organizing centers. *Proc. Natl. Acad. Sci. USA*, 81:4439–4443.

Vandre, D. D., and Borisy, G. G. 1989. Anaphase onset and dephosphorylation of mitotic phosphoproteins occur concomitantly. *J. Cell Sci.*, 94:245–258.

Verde, F., et al. 1990. Regulation of microtubule dynamics by cdc2 protein kinase in cell-free extracts of Xenopus eggs. *Nature*, 343:233–238.

Weinert, T. A. & Hartwell, L. H. (1988), The RAD9 gene controls the cell cycle response to DNA damage in Saccharomycese cerevisiae, *Science*, 241:317–322.

Wood, E. R. & Earnshaw, W. C. (1990), *J. Cell Biology*, 111:2839–2850.

Yamashiro, S., et al. 1991. Phosphorylation of non-muscle caldesmon by p34$^{cdc2}$ kinase during mitsos. *Nature*, 349:169–172.

Yamashita, K., et al., (1990), *EMBO J.* 9:4331–4338.

Zieve, G. W., et al. 1980. Production of large numbers of mitotic mammalian cells by use of the reversible inhibitor nocodazole. *Exp. Cell Res.*, 126:397–405.

Haas, R., et al. 1985. Therapiemöglichkeiten beim Hypereosinophilie-Syndrom mit Endomyocarditis fibroplastica Löffler, *Dtsch. med. Wschr.*, 110:1573–1576.

Hvizdala, E. V., et al. 1988. Lymphoblastic Lymphoma in Children-A Randomized Trial Comparing LSA$_2$-L$_2$ With the A-COP+ Therapeutic Regimen: A Pediatric Oncology Group Study, *J. Clin Oncol* 6:26–33.

Sharp, J. C., 1982. Prevention of Blastic Crisis in Ph$^1$-Positive Chronic Myeloid Leukemia, *Recent Results in Cancer Research*, 80:78–82.

Wiernik, Peter H., et al., 1979. A Comparative Trial of Daunorubicin, Cytosine Arabinoside, and Thioguanine, and a Combination of the Three Agents for the Treatment of Acute Myelocytic Leukemia. *Medical and Pediatric Oncology*, 6:261–277.

Wollner, N., et al., *Br. J. Cancer* 31 (Suppl. II):337–342, 1975.

Baccarani, M., et al., *Boll 1st Sieroter Milan* 57(3):278–288, 1978.

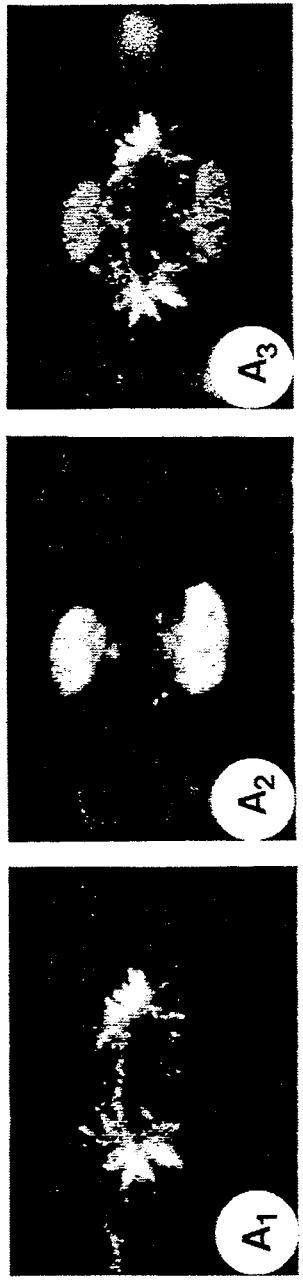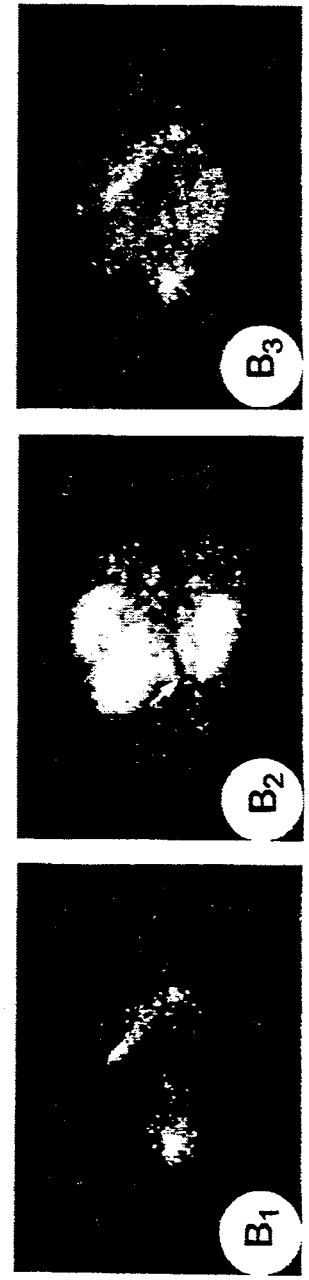
Fig. 2A. Fig. 2B. Fig. 2C. Fig. 2D. Fig. 2E. Fig. 2F.

   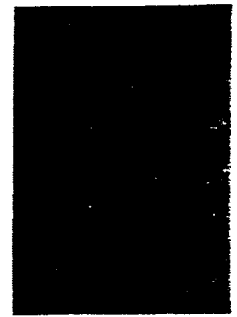
Fig. 3E. Fig. 3F. Fig. 3G. Fig. 3H.
ANTI-TUBULIN
 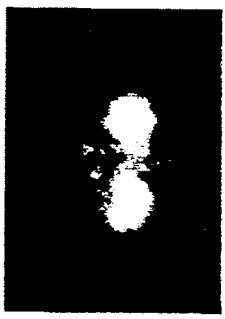 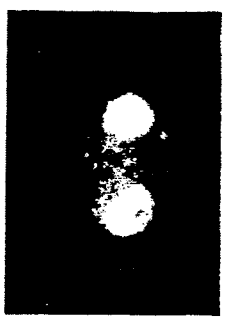 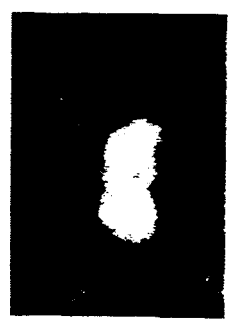
Fig. 3A. Fig. 3B. Fig. 3C. Fig. 3D.
PROPIDIUM IODIDE

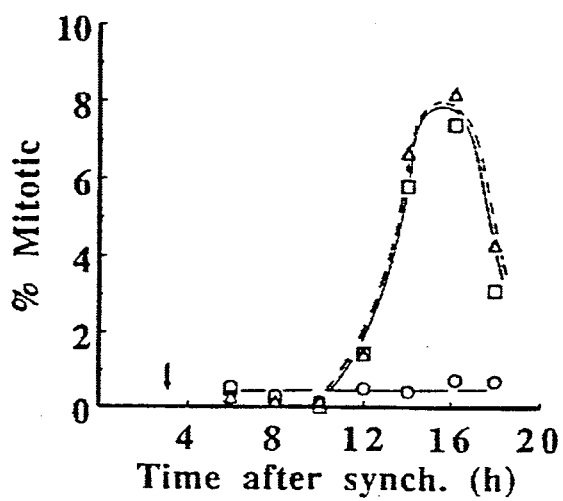
*Fig.12A.*
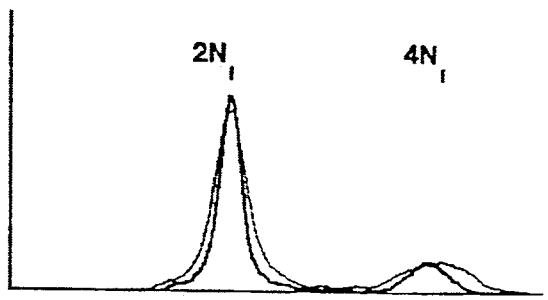
*Fig.12B.*
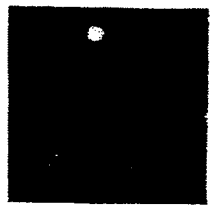   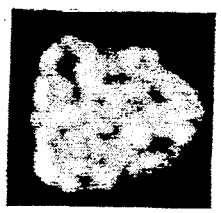   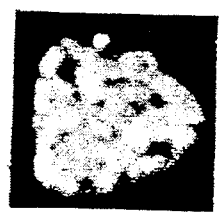
*Fig.12C.*   *Fig.12D.*   *Fig.12E.*

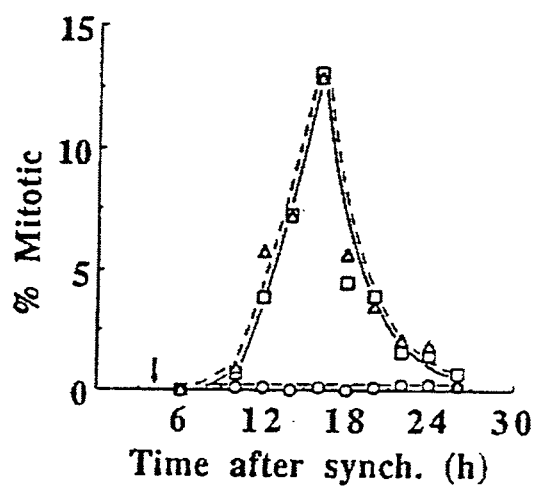
*Fig.13A.*
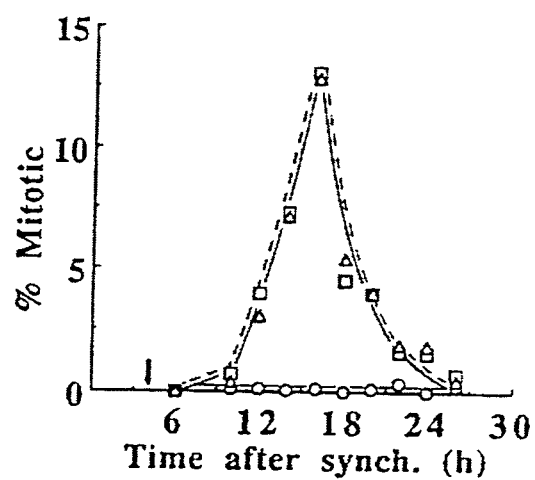
*Fig.13B.*
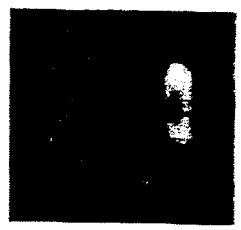 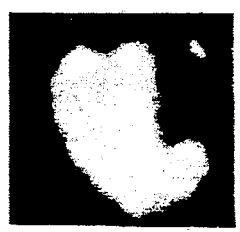 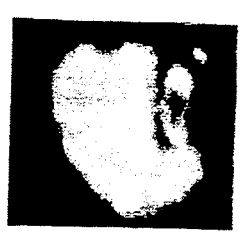
*Fig.13C.*     *Fig.13D.*     *Fig.13E.*

BINARY TUMOR THERAPY

This invention was made with government support under grants GM32022 and ESO7032 awarded by the National Institutes of Health. The government has certain rights in the invention.

TECHNICAL FIELD

The invention relates to tumor therapy, and provides a binary treatment of tumors by sequential administration of a first agent that blocks progression of the cell cycle in the tumor cells and a second agent that overrides the cell cycle block such that the tumor cells proceed past mitosis and cell death results within an additional cell cycle due to aberrant DNA replication or chromosome segregation.

BACKGROUND OF THE INVENTION

The progression of a cell through the mitotic cycle is controlled by an array of proteins. Central among them is p34$^{cdc2}$, a serine/threonine protein kinase that determines the induction of a variety of specific mitotic events (Murray and Kirschner, 1989; Nurse, 1990; Draetta, 1990). The p34$^{cdc2}$ kinase, or a closely related variant, is also involved in the induction of DNA replication in S phase (Blow and Nurse, 1990; D'Urso et al., 1990; Fang and Newport, 1991). The activity of p34$^{cdc2}$ is in turn controlled by a series of specific phosphorylation and dephosphorylation events on p34$^{cdc2}$ (Nurse, 1990), and by association of p34$^{cdc2}$ with various cyclins (Minshull et al., 1989; Reed, 1991), proteins whose abundance oscillates as the cell cycle advances.

The progression of the cell to the next stage of its cycle is under the control of factors that act as "checkpoints" which assure that the previous stage has been completed before the subsequent stage ensues (Hartwell and Weinert, 1989). The cell contains exquisitely sensitive feedback control circuits that can, for example, prevent exit from S phase if a fraction of a percent of DNA remains unreplicated (Dasso and Newport, 1990), and can block advance into anaphase in mitosis until all the chromosomes have aligned on the metaphase plate (Rieder and Alexander, 1990). The nature of these checkpoints, and how they act to block cell cycle progression, is unknown.

Various mutants have been isolated which escape specific cell cycle control circuits and progress inappropriately to the next cell cycle stage. They include wee1 mik1 double mutants (Lundgren et al., 1991), pim1 (Matsumoto and Beach, 1991), and rad9 (Weinert and Hartwell, 1988) in yeast, bimE7 in Aspergillis (Osmani et al., 1988), and the RCC1 mutant tsBN2 in mammalian BHK cells (Nishimoto et al., 1978). All of these mutants exhibit an uncoupling of entry into mitosis from the completion of DNA replication. In addition, drug treatments such as the combination of exposure to the DNA replication inhibitor hydroxyurea with exposure to caffeine can cause normal mammalian cells to enter mitosis without completing S phase (Schlegel and Pardee, 1986). Recently, mutations in *S. cerevisiae*, *bub* (Hoyt and Roberts, 1991) and *mad* (Li and Murray, 1991), have been isolated which fail to arrest in mitosis with microtubial destabilizing drugs.

The purine analogue 2-aminopurine (2-AP), a specific protein kinase inhibitor (Farrell et al., 1977; Mahadevan et al., 1990), has been shown to cause S-phase arrested cells to inappropriately enter mitosis (Schlegel et al., 1990).

We have now found that 2-aminopurine (2-AP) also causes BHK cells in mitotic arrest to rapidly exit mitosis. As the drug has the capacity to advance cells inappropriately past checkpoints at two distinct parts of the cell cycle, this result indicated that there might be an underlying common factor responsible for the various inhibitory controls of the cell cycle. We have therefore tested the capacity of 2-AP to inappropriately advance the cell cycle following cell blockage with a variety of stage specific inhibitors. We here report the striking result that 2-AP causes cells to override every cell cycle block point examined, regardless of whether the arrest point is in $G_1$, S phase, $G_2$, or mitosis. Further, it appears that cells exposed continuously to 2-AP may exit S phase without completion of replication, and may exit mitosis without metaphase, anaphase, or telophase events. Of the various cell cycle checkpoints, only one has thus far been associated with a specific molecular event. The capacity of a cell to progress from $G_2$ into mitosis is controlled by the state of phosphorylation of p34$^{cdc2}$ on a tyrosine residue (Gould and Nurse, 1989). As this p34$^{cdc2}$ phosphorylation state is specific to the $G_2$ stage of the cell cycle (Gould and Nurse, 1989), there does not appear to be a link between this inhibitory event and the checkpoints to cell cycle progression that occur in other stages of the cell cycle. Nonetheless, we now have cause to believe an underlying commonality exists, perhaps at the level of a specific 2-AP sensitive protein kinase.

Several of the inhibitors that we have used to induce cell cycle arrest (hydroxyurea, VM-26, and taxol) are used therapeutically for cancer treatment (O'Dwyer et al., 1984; Rowinsky et al., 1990). Neither drug of itself is lethal to culture cells during short exposure. However, inappropriate exit from an arrested state, induced by 2-AP, is ultimately lethal for the cell. Therefore, our results suggest that "binary" therapy, using a drug such as VM-26 or taxol in combination with 2-AP or another such purine analogue will cause inappropriate escape from cell cycle blockage, with a synergistic destructive effect on tumors.

SUMMARY OF THE INVENTION

The invention provides a method for killing a cycling cell, by contacting the cell with a first agent that blocks progression of the cell cycle in the cell, and thereafter contacting the cell with a second agent that overrides the cell cycle block such that the cell proceeds past mitosis and cell death results within an additional cell cycle due to aberrant DNA replication or chromosome segregation. The first agent blocks the progression of the $G_1$, S, $G_2$, or mitosis stage of the cell cycle. The second agent is preferably 2-aminopurine (2-AP) or 6-dimethylaminopurine (6-DMAP). The duration of contact with the first agent is advantageously limited to a first time period sufficient to block the progression of the cell cycle, and the duration of contact with the second agent is limited to a second time period sufficient to override the cell cycle block.

The invention also provides a method of screening for a binary tumor therapy agent, by contacting a cycling mammalian cell with a first agent that blocks progression of the cell cycle, preferably mitosis, in the cell; thereafter contacting the cell with a candidate second agent; and determining that the candidate second agent is a binary tumor therapy agent if the candidate second agent overrides the cell cycle block such that the cell proceeds past mitosis and cell death results within an additional cell cycle due to aberrant DNA replication or chromosome segregation.

BRIEF DESCRIPTION OF THE DRAWINGS

FIGS. 2A–2L presents photomicrographs showing that condensed mitotic chromosomes fail to form during mitosis in 2-AP, and that uncondensed chromatin is deformed by the mitotic spindle;

FIGS. 3A–3H presents serial sections of a toroid nuclear body, as described in the First Series of Examples;

FIGS. 12A–12E shows that 2-AP overrides mimosine-dependent $G_1$ blockage;

FIGS. 13A–13E shows override of hydroxyurea or aphidicolin S-phase block by 2-AP;

DETAILED DESCRIPTION OF THE PREFERRED EMBODIMENT

Figures 1A, 1B, 1C, 1D:
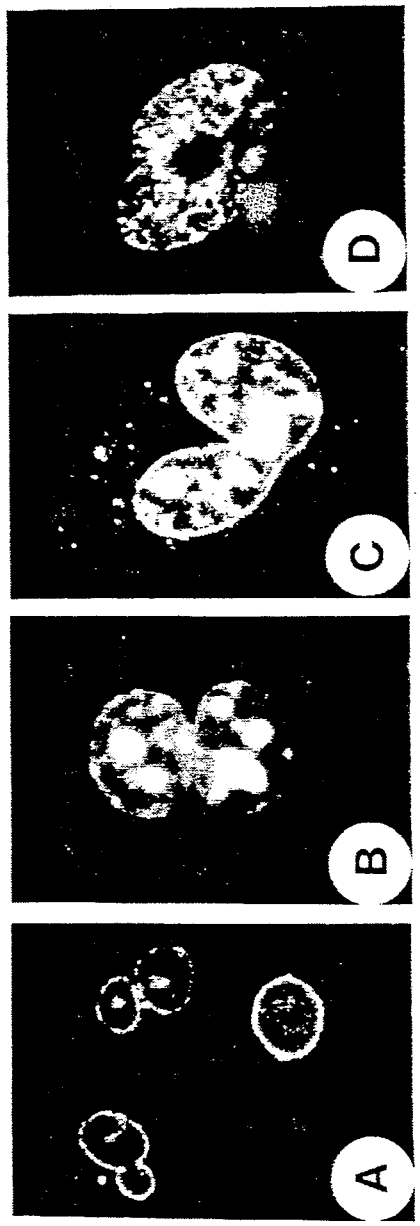
FIGS. 1A to 1D presents photomicrographs showing nucleus morphologies observed following 2-AP treatment of cycling BHK cells.

We have found that the purine analogues, 2-aminopurine (2-AP) and 6-dimethylaminopurine (6-DMAP), cause mammalian cells that are blocked in mitosis with nocodazole to rapidly exit mitosis. Nocodazole is one of a class of drugs that causes arrest of cells in mitosis through interference with the function of microtubules, which are protein polymers that are important to the mitotic process. In nocodazole, the mammalian cells that were used (baby hamster kidney, BHK) remain arrested in mitosis for a period of time in excess of one day. When 2-AP or 6-DMAP is added to these arrested cells, 70 to 100% exit from mitosis within a time course of less than one hour (see below). 2-AP- or 6-DMAP-induced exit from mitosis is aberrant, in that cells enter an effective interphase without completing a functional, normal mitosis.

We have found that prolonged exposure to either 2-AP or to nocodazole is not lethal to the majority of cells. However, exposure of cells to the combination of the two drugs in the regimen indicated above quickly leads to a lethal state.

Nocodazole is similar in action to two drugs currently used either routinely (vinblastine and its congeners), or experimentally (taxol), for the treatment of a variety of human tumors. Both vinblastine and taxol are effective against certain tumors by apparently arresting cells at the point of mitosis in their cell cycle, rather than directly causing cell death. Presumably, these drugs are effective because tumor cells are more sensitive to these drugs and arrest more readily in mitosis at low drug concentrations than do the patient's normal cells.

Taxol has recently been shown to be effective against breast and ovarian cancers, and against melanomas, in human trials. We have now tested cells blocked with taxol, and we have found that the combination of taxol arrest in mitosis with a following short exposure of the taxol-arrested cells to 2-AP leads to rapid exit from mitosis and apparent cell death (see below). Vinblastine is effective against some human tumors, including certain leukemias and lymphomas. We expect to observe a similar mitotic exit and death of vinblastine-arrested cells, when exposed to 2-AP.

We have found that the effect of 2-AP or 6-DMAP extends beyond the mitotic stage of the cell cycle, and is general for overriding drug-induced arrest at all stages of the cell cycle tested. Cells blocked in the $G_1$ phase of the cell cycle by the drug mimosine, or in S-phase by hydroxyurea, aphidicolin, or methotrexate, or in $G_2$ phase by the podophyllotoxin analogue VM-26 are all caused to override their cell cycle block and proceed aberrantly to subsequent phases of the cell cycle. Thus, each of these arrested cells will arrive in mitosis on schedule, compared to untreated control cells, after exposure to 2-AP (see below), as though the cell had been removed from the blocking agent. However, the normal cell metabolic function that is suppressed by each of these drugs remains suppressed in 2-AP and in 6-DMAP, and the exit from the arrest point is therefore aberrant.

VM-26, the $G_2$ phase blocking agent, is currently used in tumor therapy. VM-26 alone does not appear to be lethal to cells over the time course of our experiments on BHK cells in culture, but following exposure to 2-AP, after allowing a brief time for VM-26 arrest in $G_2$, the combined VM-26 and 2-AP drug exposure is lethal to BHK cells.

As noted above, we have found that the purine analogues 2-AP and 6-DMAP do not interfere with the cell cycle when given alone, that is, in the absence of cell cycle arrest drugs. It is thus apparent that 2-AP and 6-DMAP are not of themselves highly lethal to randomly cycling cells based on short-term exposures. It is also apparent that current tumor therapy drugs, such as VM-26, taxol, and vinblastine, arrest cells in distinct parts of the cell cycle rather than effect a rapid cell death. However, the combination of arrest in the cell cycle by VM-26, taxol, or vinblastine followed by aberrant override of cell cycle arrest by 2-AP or 6-DMAP is quickly lethal to the majority of cells in culture.

The drugs VM-26, taxol, and vinblastine are apparently useful in chemotherapy because certain tumor cell types are more sensitive to them than are normal cells.

The invention accordingly provides a combination tumor therapy, employing the already demonstrated effective arrest of tumor cells with an agent such as VM-26, taxol, or vinblastine. After cells are arrested, the blocking drug is combined with a brief exposure to a purine analogue that effects a cell cycle override leading to cell death. We call this protocol "binary therapy," as the combination of drugs in the proper sequence is synergistic and much more effective than treatment with either agent alone.

This protocol extends to any purine analogue (i.e., a compound containing a substituted purine [imidazo (4,5-d) pyrimidine] ring system) or other second agent with a similar override effect on cell cycle blockage. Such analogues and agents can be readily screened and selected (as described herein) for effectiveness and optimum performance in patients as compared with those we have used (2-AP and 6-DMAP) to make these seminal observations.

The subject binary therapy procedure utilizes drugs already known to be effective against human tumors (e.g., VM-26, taxol, and vinblastine) and makes their use much more effective. The protocol is simple in theory and practice: One drug serves to arrest and accumulate cells at a point in the cell cycle where they are sensitive to the action of the other drug, and the second drug is lethal only to cells, on brief exposure, whose cell cycle progress has been arrested by the first drug.

The subject method for killing a cycling cell includes the steps of: contacting the cell with a first agent that blocks progression of the cell cycle in the cell; and thereafter contacting the cell with a second agent that overrides the cell cycle block such that the cell proceeds past mitosis and cell death results within an additional cell cycle due to aberrant DNA replication or chromosome segregation. By a cycling cell is meant a cell, such as a proliferating cancer cell, that is committed to pass through the S, $G_2$, and M (mitosis) phases of the cell cycle.

The first agent may be selected from among agents that block the progression of the $G_1$, S, $G_2$, and/or mitosis stages of the cell cycle. Such cell arrest agents are known and used for antineoplastic therapy; see generally: The Merck Manual, Fifteenth Edition, Ch. 105, 1987. Representative of such first agents are drugs that block the $G_1$ stage (e.g., mimosine), drugs that block the S stage (e.g., inhibitors of ribonucleotide reductase, inhibitors of DNA polymerase-$\alpha$, inhibitors of dihydrofolate reductase, and alkylating agents), drugs that block the $G_2$ stage (e.g., topoisomerase II inhibitors), and drugs that block mitosis (e.g., microtubule inhibitors). Representative S-phase inhibitors include the ribonucleotide reductase inhibitor aphidicolin, the DNA polymerase-$\alpha$ inhibitor hydroxyurea, the dihydrofolate reductase inhibitor methotrexate, and alkylating agents such as nitrogen mustards, nitrosureas, and bleomycins. Representative first agents that block the $G_2$ stage include the topoisomerase II inhibitors VM-26 (teniposide) and VP-16 (etiposide). However, the first agent preferably blocks mitosis. Representative microtubule inhibitors for this purpose include nocodazole, taxol, and vinca alkaloids such as vincristine and vinblastine.

The second agent is generally characterized as effecting an inappropriate override of the cell cycle block caused by the first agent, leading to abnormal mitosis, either in the cell cycle in which the first and second agents are administered or in the next cell cycle (of the daughter cells), and cell death due to aberrent DNA replication or chromosome segregation. Candidate second agents for this purpose are purine analogues that inhibit protein kinase activity, and particularly 2-aminopurine (2-AP) and 6-dimethylaminopurine (6-DMAP). Other second agents can be readily identified and selected by a screening protocol including the following steps: contacting a cycling mammalian cell with a first agent that blocks progression of the cell cycle in the cell; thereafter contacting the cell with a candidate second agent; and selecting the candidate second agent for use in the subject binary tumor therapy if the second agent overrides the cell cycle block such that the cell proceeds past mitosis and cell death results within an additional cell cycle due to aberrant DNA replication or chromosome segregation. In this screening protocol, the first agent may block the progression of the $G_1$, S, $G_2$, or mitosis stages of the cell cycle. However, the first agent preferably blocks the mitosis stage, as this affords a quick, convenient, and highly diagnostic system for observing the requisite override effects of the second agent.

In clinical practice, the first agent is administered using established protocols. However, in the subject binary therapy, the duration of patient contact with the first agent may be advantageously limited to a first time period sufficient to block the progression of the cell cycle in the targeted tumor cells. The condition of cell cycle arrest can be monitored by known procedures, including tumor biopsy and determination of mitotic index or cell cycle stage-specific immunochemical markers. The first time period for establishing the desired degree of tumor cell cycle arrest will vary with individual patients and may be on the order of 8 to 12 hours.

Furthermore, the duration of patient contact with the second agent is advantageously limited in the subject binary therapy to a second time period sufficient only to override the cell cycle block in the targeted tumor cells. This condition can be conveniently assessed by monitoring the secondary cell-killing effects. e.g., by monitoring tumor shrinkage by CAT scan or biopsy, or by monitoring serum content of indicative cell products such as diagnostic immunoglobulins or tumor cell antigens. This second time period is generally less than the first time period, on the order of up to several (e.g., three to five) hours as determined on such a patient-specific basis. In treatments using a first agent that blocks mitosis, the second time period is relatively short, e.g., on the order of 5 to 60 minutes, particularly where the second agent is directed by catheterization to the tumor site.

FIRST SERIES OF EXAMPLES

The protein kinase inhibitor 2-aminopurine (2-AP) inhibits a subset of mitotic events in BHK cells. In the presence of the drug, these cells form a bipolar spindle in mitosis, but chromatin fails to generate functioning chromosomes. Cells in 2-AP progress through a partial mitosis, in which there are no observable metaphase, anaphase, or telophase events. After 12 hours of exposure to 2-AP the chromatin in mitotic cells fails to condense into discrete chromosomes, and is displaced by the spindle to form "binucleate" cells and cells containing abnormally shaped nuclei in the subsequent interphase. Other mitotic modifications of nuclei, such as nucleolar and nuclear lamina disassembly, occur normally. Centromeres in these nuclei do not become engaged in the spindle, but instead show either no association or a lateral arrangement around the spindle. Cells treated with 2-AP are not arrested in mitosis. Therefore, mitotic exit is not inhibited by the failure of these cells to progress through the latter stages of mitosis. Further, nocodazole-arrested cells quickly exit mitotic arrest when 2-AP is added. We conclude that 2-AP interferes with a specific subset of mitotic events, and that it allows cells to overcome checkpoints that require spindle function for mitotic progression.

Materials and Methods

Cell culture and synchronization: Baby Hamster Kidney (BHK) cells were grown as monolayers in Dulbecco's Modified Eagle's Medium (Gibco Laboratories, Grand Island, N.Y.) supplemented with 10% defined fetal bovine serum (Hyclone Laboratories, Logan, Utah.), and were maintained in a humid incubator at 37° C. in a 5% $CO_2$ environment. Cells were synchronized in mitosis by addition of nocodazole (Sigma Chemical Co., St. Louis, Mo.) to a final concentration of 0.06 µg/ml, from a 20 µg/ml stock in dimethylsulfoxide.

Antibodies: Anti-lamin B human autoimmune serum (Guilly et al. 1987a), a gift of Dr. J-C Courvalin (Gif-sur-Yvett, France), was used at a 200-fold dilution. Anti-centromere serum from a human patient (J. D.) with a CREST sceleroderma autoimmune disorder was supplied by Dr. Barbara Hamkalo (University of California at Irvine) and used at a 500-fold dilution. MPM-2-mouse monoclonal antibody, reactive with mitosis-specific phosphoproteins (Davis et al. 1983), was supplied by Dr. P. N. Rao (University of Texas), and was used at a 500-fold dilution of the ascites fluid. Mouse anti-$\beta$-tubulin antibody (Eastacres Biologicals, Southbridge, Mass.) was diluted 25-fold for use.

Immunofluorescence microscopy: In preparation for microscopy, cells were grown for a minimum of 12 hours on polylysine-coated glass coverslips. Unless other wise noted, cells were fixed for 20 minutes with 2% paraformaldethyde in PBS (136 mM NaCl, 2 mM KCl, 10.6 mM $Na_2PO_4$, and 1.5 mM $KH_2PO_4$, pH 7.4) at 37° C. The coverslips were then washed 3 times, 5 minutes each, with PBS. Primary and secondary antibodies were applied in PBS, also containing 3% bovine serum albumin, 0.05% Tween-20, and 0.1% sodium azide. Incubation with primary antibodies (60 minutes in a humid chamber at 37° C.) was followed by three washes with PBS, as above. Secondary antibodies were then applied for 30 minutes at 37° C. in a humid chamber. They included FITC-conjugated affinity-purified goat anti-human and anti-mouse antibodies, applied at 8.5 µg/ml, and Texas Red-conjugated goat anti-mouse antibodies, applied at 14 µg/ml. All secondary antibodies were from Tago, Inc. (Burlingame, Calif.). Coverslips were then washed twice with PBS both before and after a 5 minutes incubation with propidium iodide (1 µg/ml in PBS), or three times in PBS if propidium iodide staining was omitted.

MPM-2 antibody was applied to cells as described above, except that cells were precleared and fixed according to the technique of Vandre and Borisy (1989). Cells were permeabilized 90 seconds with 0.5% Triton X-100 in PHEM (60 mM Pipes, 25 mM Hepes, 10 mM EGTA, 2 mM $MgCl_2$, pH 6.9) at 37° C. and then fixed 15 minutes with 0.7% glutaraldehyde in PHEM at 37° C. Following a PBS wash, autofluorescence was quenched by two 15 minute reductions with 1 mg/ml $NaBH_4$ in 10 mM Tris-HCl, 125 mM NaCl, pH 7.2. Coverslips were then washed 3 times with PBS, and the antibody incubations and washes were thereafter as described above.

For microscopy, coverslips were mounted with 25 mg/ml 1,4-diazabicyclo(2.2.2)octane (Kodak, Rochester, N.Y.) in 90% glycerol/PBS, pH 8.6 (Johnson et al. 1982), and samples were observed using a MRC-500 Laser Scanning Confocal apparatus (Bio-Rad Microscience, Cambridge, Mass.) attached to a Nikon Optiphot microscope (Nikon, Inc., Torrance, Calif.). Photographs were taken on Ilford XP1 400 film (Ilford Ltd., Cheshire, England) at an exposure of f5.6, for one second. Prints were made on Ilford MC Rapid paper (Ilford).

2-Aminopurine treatment: 2-Aminopurine was obtained from Sigma Chemical Company (St. Louis, Mo.) as either a free base or a nitrate salt. A stock of 100 mM 2-AP was kept in 100 mM Hepes buffer at pH 7.2. In experiments where 2-AP was applied, control cells received the identical final concentration (10 mM) of Hepes buffer.

Results

After 12 hours of exposure to 2-aminopurine (2-AP), a substantial proportion of baby hamster kidney (BHK) cells appear binucleate (FIG. 1A), and one's first impression on observing these cells is that the presence of 2-AP has caused the cells to abort in cytokinesis. Many 2-AP-treated cells appear truly binucleate on close examination (FIGS. 1A and 1B). However, many of the cells in a population treated with 2-AP are not binucleate, but contain a single nucleus with various characteristic distortions in shape. Of these, a substantial number of cells have a lobed nucleus, with the two lobes connected by a narrow isthmus of nuclear material (FIGS. 1B and 1C). Another rarer distortion is a toroid, or doughnut-shaped, nucleus (FIG. 1D). Among other morphologies observed are interphase nuclei with multiple lobes, or asymmetric lobes (FIG. 1A, and data not shown). We will show that the origin of these distorted nuclei is due to a "partial mitosis" rather than a failure of cytokinesis. Partial mitosis is defined as the failure of cells containing a mitotic spindle to form functioning chromosomes, and by the exit of these cells from mitosis without a metaphase, anaphase, or telophase.

Referring to FIG. 1 in particular detail, the nuclear morphologies were observed following 2-AP treatment as follows. Cycling BHK cells were treated with 10 mM 2-AP for 12 hours, then fixed and processed for immunofluorescence as described above. All images are horizontal optical sections (0.2 µm) generated by confocal microscopy. (A) Cells stained with anti-lamin antibody, showing a normal appearing mononucleate cell, a binucleate cell, and a cell with an asymmetrically lobed nucleus. (B-D) Cells visualized with propidium iodide stain. (B) Cell with a symmetrically lobed single nucleus, connected by a narrow bridge. (C) Cell with a more prominent and asymmetric lobe. (D) Cell with a toroid nucleus.

Partial mitosis in 2-AP-treated cells: After 12 hours of exposure to 2-AP, one can readily identify a subpopulation of treated cells in mitosis, as defined by anti-tubulin staining. These cells have lost their interphase tubulin array and instead display the tight astral foci of microtubules and the bipolar spindle arrays characteristic of mitosis (FIG. 2). The proportion of the cell population with mitotic microtubule arrays remains at a constant 4–5% of the total through 12 hours, which is not appreciably different from the mitotic index of untreated cells (see FIG. 10).

When counterstained with propidium iodide, 2-AP-treated mitotic cells exhibit a remarkable chromatin morphology. Although mitotic spindles are present, chromatin is not condensed into discernable chromosomes, but remains a contiguous body (FIG. 2). We term such chromatin in otherwise mitotic cells "nuclear bodies." Some mitotic character is apparent in these mitotic nuclear bodies, in that they contain no apparent nucleoli, as determined by the lack of distinctive nucleolar staining with propidium iodide (FIG. 2), and by the failure of nuclei to stain with anti-nucleolar antibodies (data not shown). The chromatin appears somewhat condensed relative to interphase nuclei, but never displays discrete chromosomal structures.

Figure 2G:
Figure 2H:
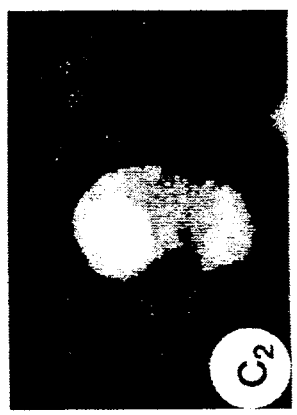
Figure 2I:
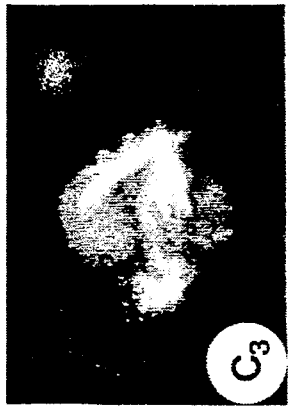
Figure 2J:
Figure 2K:
Figure 2L:
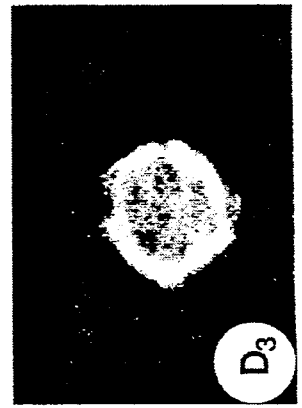

Optical sectioning with a confocal microscope reveals that, in 2-AP-treated cells in mitosis, nuclear bodies are displaced laterally or are pierced by spindle microtubules. The displacement of the nuclear bodies in mitotic cells yields distinctive polymorphic nuclei. In one class of mitotic cell, one finds a bipolar spindle lying between two spherical nuclear bodies laterally arranged on either side of the spindle (FIG. 2A). Other commonly observed classes include mitotic nuclear bodies pierced by narrow channels which contain spindle microtubules, and have a sharp boundary of chromatin bordering the channel (FIG. 2B). Also, there are kidney-shaped nuclear bodies (FIG. 2C), or nuclear bodies with two or more lobes connected by a narrow isthmus of chromatin crossing the spindle equator (see FIG. 1B for an interphase cell with this nuclear configuration). One occasionally finds toroid nuclear bodies. In these cells, the central overlap zone of the bipolar spindle appears to puncture through to the center of the mitotic nuclear body to create a doughnut or torus shape. Serial optical sections of one such mitotic cell are shown in FIG. 3.

Referring to FIG. 2 in more detail, condensed mitotic chromosomes fail to form during mitosis in 2-AP, and uncondensed chromatin is deformed by the mitotic spindle. (A-C) Mitotic BHK cells from a cycling population, treated with 2-AP for 12 hours, and (D) a similarly processed mitotic control are shown stained with anti-tubulin (left column), counter-stained with propidium iodide (middle column), and as merged images (right column). A, B, and D are horizontal optical sections, while C is a projection generated by summation of serial horizontal sections. Propidium iodide staining shows a lack of discrete chromosomes in 2-AP-treated cells ($A_2$, $B_2$, $C_2$). (A) Chromatin is displaced laterally by the spindle into two discrete nuclear bodies. (B) Microtubules pierce the chromatin and form narrow channels through it (arrow). (C) A kidney-shaped nuclear body surrounds the spindle. (D) In a control cell, metaphase chromosomes are aligned at the center of the spindle.

FIG. 3 shows serial sections of a toroid nuclear body. Selected horizontal 0.2 μm sections through a mitotic cell are shown, proceeding from top to bottom at intervals of 0.6–0.8 μm. Anti-tubulin indirect immunofluorescent staining is shown in the left-hand column, and propidium iodide staining of DNA is shown at right. The chromatin is discontinuous only in the central horizontal sections of the cell, where microtubules penetrate the nuclear body.

Figure 4A:
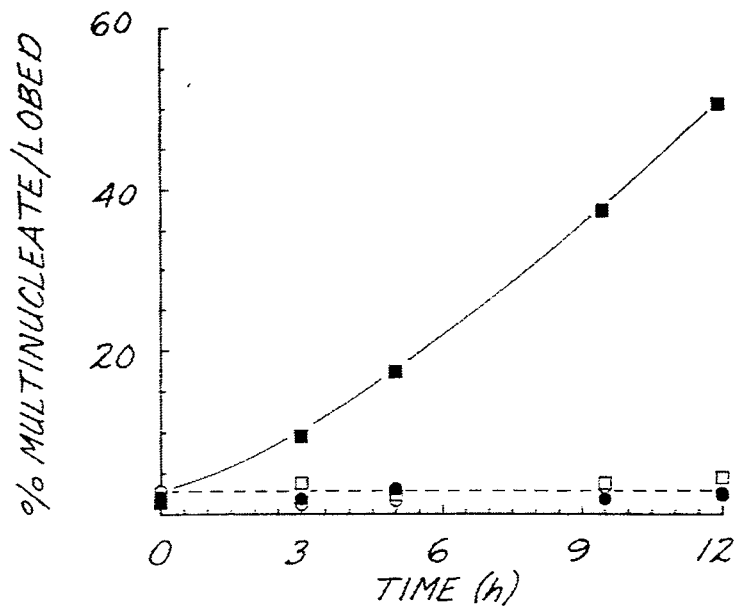
FIGS. 4A–4C shows that accumulation of multinucleate and lobed nuclear cells is linear with time during 2-AP treatment, but is prevented by the presence of nocodazole.
Figure 4B:
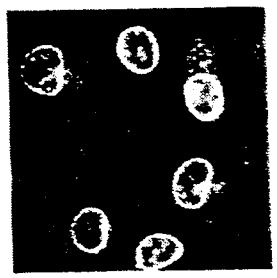

Such images of 2-AP-treated mitotic cells suggest that the mitotic spindle actively deforms the nuclear body. In support of this conclusion, a quantitative analysis of the proportion of the 2-AP-treated cells with distorted nuclei shows that the percentage of the population with apparent binuclear appearance (including lobed nuclei) rises linearly to approximately 50% of the population over 12 hours of exposure to the drug (FIG. 4A). The rate of accumulation of "binucleate" cells is similar to the rate of accumulation of cells in mitotic arrest following exposure to nocodazole (see FIG. 10), consistent, with a requirement for passage through mitosis in order to form distorted nuclei. The requirement for a mitotic spindle to create distorted nuclei is also supported by our observation that simultaneous exposure to nocodazole prevents formation of binucleate cells by 2-AP, causing cells to remain mononucleate over 12 hours of drug exposure (FIGS. 4A and 4B).

Figure 4C:
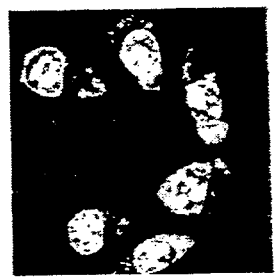

Referring to FIG. 4 in more detail, accumulation of multinucleate and lobed nuclear cells is linear with time during 2-AP treatment, but is prevented by the presence of nocodazole. (A) Multinucleate/lobed nuclear cells accumulate during treatment with 10 mM 2-AP (closed squares), but not when treated either with nocodazole (closed circles), or nocodazole plus 2-AP (open squares). Untreated controls (open circles) are also shown. Nuclear morphology was assayed both by epifluorescence with anti-lamin B antibodies, and by propidium iodide staining. All points represent the average of three independent counts of greater than 100 cells each. Standard deviation was less than 2.5% of the ordinate for all data points. (B) Cells treated for 12 hours with nocodazole and 2-AP remain mononucleate, as assayed by anti-lamin B (upper frame), and by propidium iodide (lower frame).

It is worth noting that binucleate cells begin accumulating immediately upon exposure to 2-AP (FIG. 4). This observation suggests that the partial mitotic effect of 2-AP results from the drug acting directly on mitosis and does not result from mutagenic effects of 2-AP (Caras et al. 1982; Schaff et al. 1990; Speit et al. 1990) during S-phase. However, some effect of S-phase on chromatin behavior is suggested by observations (data not shown) that some M-phase cells have distinct but nonfunctioning chromosomes after short times of exposure (3 hours) to 2-AP.

The mitotic spindle that forms in 2-AP-treated cells (FIGS. 2A, 2B, and 2C) is characteristically narrower than the typical spindle found in untreated cells (FIG. 2D) and usually has a more prominent array of astral microtubules. This morphology possibly arises due to lack of stabilization of kinetochore microtubules by chromosome capture (Mitchison and Kirschner, 1985; Hayden et al. 1990). Nonetheless, it appears that discrete chromosomes may not be required in order to generate a bipolar spindle morphology in these cells.

Figure 5A:
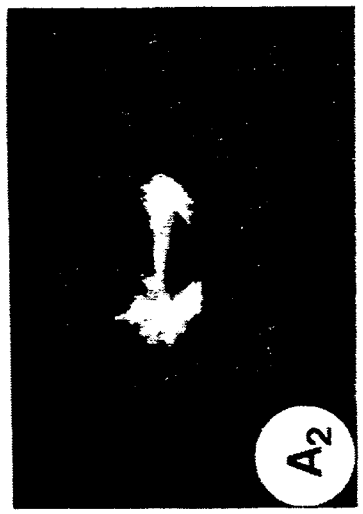
FIGS. 5A and 5B presents photomicrographs showing distribution of lamin B in 2-AP-treated mitotic cells.

Mitotic progression in 2-AP: Upon entry into mitosis, the lamin proteins that demarcate the nuclear periphery disassemble. Lamin B undergoes a $p34^{cdc2}$ kinase-specific phosphorylation that has been functionally linked to nuclear lamina breakdown (Peter et al. 1990b). From in vitro model systems with Xenopus oocytes, it is evident that lamin disassembly can be temporally distinct from both chromosome condensation and nuclear envelope dissolution (Newport and Spann, 1987). In 2-AP-treated cells identified as mitotic by the presence of a mitotic spindle, lamin B has generally disappeared from the periphery of the nuclear bodies (FIG. 5), although in some rare cases, a remnant of the lamin border can be detected on nuclear bodies in mitotic cells (see FIG. 5A, arrow). Interphase cells in 2-AP, in contrast, contain intact lamin B borders around their nuclei (see FIG. 1A). It is not known whether mitotic nuclear bodies retain a distinct semipermeable border in the absence of lamin B. However, where microtubules of the spindle appear to pierce through the interior of the nuclei, one always finds a distinct boundary separating the polymer from the nuclear interior (see FIG. 2B).

Figure 5B:

Referring to FIG. 5 in more detail, distribution of lamin B in 2-AP-treated mitotic cells is shown. The continuous rim of lamin B that forms the boundary on interphase nuclei (see FIG. 1A) is largely dispersed throughout the cytoplasm in 2-AP-treated mitotic cells ($A_1$). Small amounts of residual lamin B (arrow) sometimes remain associated with the chromatin border (chromatin is the clear zone in $A_1$). The cell is identified as mitotic by the presence of a mitotic spindle ($A_2$), detected with anti-tubulin antibodies.

Figure 6A:
FIGS. 6A–6D shows distribution of MPM-2 epitopes in 2-AP-treated mitotic cells.
Figure 6B:
Figure 6C:
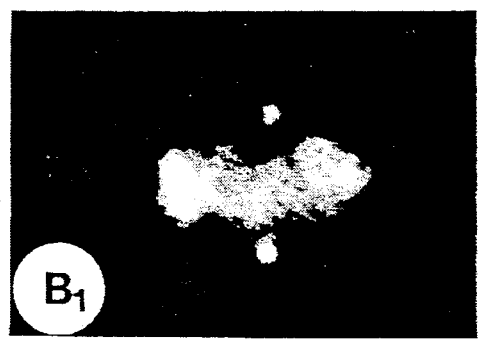
Figure 6D:

We have also assayed for the distribution of the mitosis-specific antigen MPM-2, which has been shown to represent mitosis-specific phosphorylation of a subset of mitotic proteins (Davis et al. 1983). MPM-2 antigens are normally present in the cytoplasm of mitotic cells, and are detected localized to centrosomes and chromosomes following removal of soluble proteins by cell lysis (Vandre et al. 1984) (FIG. 6B). Exposure of cells to 2-AP has no effect on the intensity of the cytoplasmic signal (data not shown), and centrosome staining by MPM-2 antibody is readily detected in all lysed 2-AP-treated mitotic cells (FIG. 6A). Staining of chromatin by MPM-2 antibody also occurs but, as might be expected from the lack of distinct chromosomes, is diffuse and evenly distributed throughout the nuclear body. We conclude that 2-AP does not apparently alter the presence or distribution of phosphorylated MPM-2 substrates.

Referring to FIG. 6 in more detail, distribution of MPM-2 epitopes in 2-AP-treated mitotic cells is shown. The distribution of MPM-2 epitopes, representative of mitosis-specific phosphorylation antigens, was examined by both 2-AP-treated (A) and untreated control cells (B) that were cleared by permeabilization with 0.5% Triton X-100, and then fixed for immunofluorescence. MPM-2 antigen distribution is shown in $A_1$, $B_1$, and propidium iodide stain for chromatin is shown in $A_2$, $B_2$. In both treated and control cells, MPM-2 epitopes occur at the centrosomes, and on the chromatin or chromosomes. In the 2-AP-treated cell shown, the chromatin is displaced laterally by the spindle, and the centrosomes ($A_1$, upper and lower spots) are perpendicular to the axis of the two separated chromatin bodies ($A_2$).

We have presented images of mitotic cells in 2-AP showing the absence of condensed chromosomes, and the lack of distinct mitotic stages. A quantitation of the mitotic stages observed in 2-AP cells in mitosis versus the distribution of mitotic stages in control cells (TABLE 1) demonstrates unequivocally the complete failure of 2-AP-treated cells to progress through the normal stages of mitosis. No cell observed to be in mitosis, as defined by the presence of a mitotic spindle, gives evidence of normal mitotic chromosomes, or of chromatin aligned as for metaphase or later stages of mitosis. All the surveyed cells contain a spindle and a discrete nuclear body with chromatin that has failed to condense into individual chromosomes.

TABLE 1

| Progression of 2-AP Treated Cells through Mitosis | | |
|---|---|---|
| | 2-AP (%) | Control (%) |
| Prophase Nuclear bodies (no chromosomes): | | |
| Bifurcated | 27.7 ± 2.0% | 0.0% |
| Lobed | 62.4 ± 2.5% | 0.0% |
| Undeformed | 9.6 ± 0.7% | 0.0% |
| Chromosomes | 0.3 ± 0.5% | 37.3 ± 0.5% |
| Metaphase | 0.0% | 40.8 ± 0.3% |
| Anaphase | 0.0% | 9.3 ± 1.3% |
| Telophase | 0.0% | 12.5 ± 0.9% |

Referring to TABLE 1, all values represent percentage of mitotic cells, as scored by the presence of a mitotic spindle detected by immunofluorescence with anti-tubulin antibodies after exposure to 2-AP for 12 hours. Stages of mitosis were classified by the distribution of DNA stained by propidium iodide, relative to the spindle. Metaphase was defined as the alignment of chromosomes/chromatin in a plate at the center of the spindle, and anaphase as chromosomes/chromatin separated in two distinct sets along the axis between the poles. Telophase was defined by the presence of a cleavage furrow, detected by propidium iodide staining of cytoplasmic RNA. All other distributions of DNA are designated as prophase. Values are averages of 3 counts of 100 or more cells each.

Figure 7A:
FIGS. 7A–7I presents photomicrographs showing that centromeres interact abnormally with the spindles of 2-AP-treated cells.
Figure 7B:
Figure 7C:
Figure 7D:
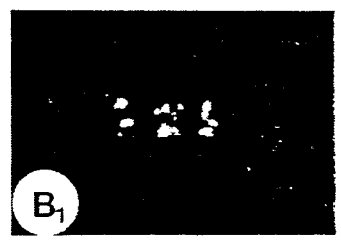
Figure 7E:
Figure 7F:
Figure 7G:
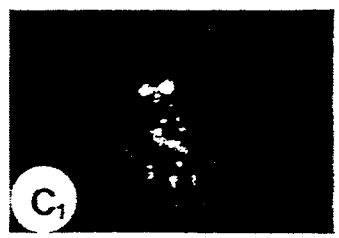
Figure 7H:
Figure 7I:
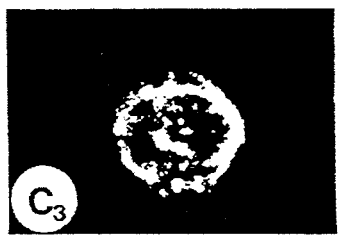

Using anti-centromere antibodies one finds that the centromeres of mitotic 2-AP-treated cells are often dispersed at random in the mitotic nuclear bodies and do not appear to interact with the spindle (FIG. 7A), in contrast to the characteristic integration of centromeres into the spindle in control cells (FIG. 7C). However, a number of mitotic nuclear bodies exhibit centromeres clustered in a "shell" at the periphery of the spindle (FIG. 7B), giving evidence of an apparent limited capacity of centromeres in some cells to associate with microtubules.

Referring to FIG. 7 in more detail, centromeres interact abnormally with the spindles of 2-AP-treated cells. During mitosis in the presence of 2-AP, centromeres do not align as for metaphase or anaphase, but instead show either no association with the spindle as in (A), or form a shell around the outside of the spindle, as in (B). For contrast, centromere alignment in a typical metaphase array is shown in an untreated mitotic cell (C). For each cell, anti-centromere indirect immunofluorescence staining is shown in the left column, anti-tubulin staining is shown in the center column, and a merge of the anti-centromere and anti-tubulin images is shown in the right column.

Figures 8A, 8B, 8C:
FIGS. 8A–8C presents photomicrographs showing that chromosomes present in cells released from a nocodazole block into 2-AP do not engage in the mitotic spindle.

Mitotic behavior of nocodazole-treated cells in 2-AP: As randomly cycling cells exposed for 12 hours to 2-AP contain only relatively decondensed chromatin during mitosis, it cannot be ascertained by observing these cells whether the bipolar spindle could engage chromosomes if they were present, and permit normal mitotic function. To create this experimental condition, cells were blocked in mitosis with nocodazole and released from nocodazole block into 2-AP. In these cells, chromosomes persist for at least 20 minutes but appear to have no capacity to become engaged in the bipolar spindle that forms (FIG. 8). In a subset of cells, the chromosomes remain as a spherical shell around an aster before they decondense. In the remainder, chromosomes either border each side of the spindle, as shown here (FIG. 8), or surround the spindle in a "figure of 8" pattern. Centromeres appear to lie proximal to the spindle on its periphery (data not shown), reminiscent of the frequently observed proximal orientation of centromeres on spindles in cells treated with 2-AP alone (FIG. 7B). In no case have we observed chromosome or centromere orientations that suggest metaphase or anaphase in these cells. Finally, when these cells reenter interphase, they often have H-shaped or "figure of 8" nuclei. In contrast, control cell released from nocodazole block proceed through a normal mitosis (data not shown).

Referring to FIG. 8 in more detail, chromosomes present in cells released from a nocodazole block into 2-AP do not engage in the mitotic spindle. Cells were blocked with nocodazole for 12 hours, recovered from blockage by washing into fresh medium, and 10 mM 2-AP was added. After 40 minutes in 2-AP, the cells were fixed and processed for indirect immunofluorescence. ($A_1$) Chromosomes stained with propidium iodide; ($A_2$) anti-tubulin counterstain of same cell. ($A_3$) Merged image of propidium iodide and anti-tubulin stain, demonstrating that the chromosomes lie adjacent to the spindle.

Figures 9A, 9B:
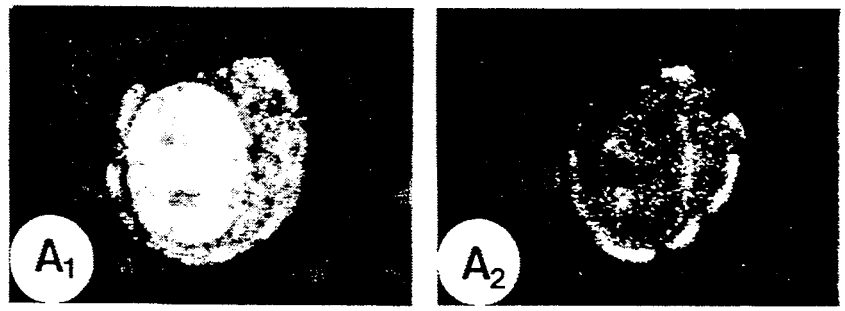
FIGS. 9A–9D presents photomicrographs showing nuclear reformation following the addition of 2-AP to nocodazole-blocked cells.
Figures 9C, 9D:
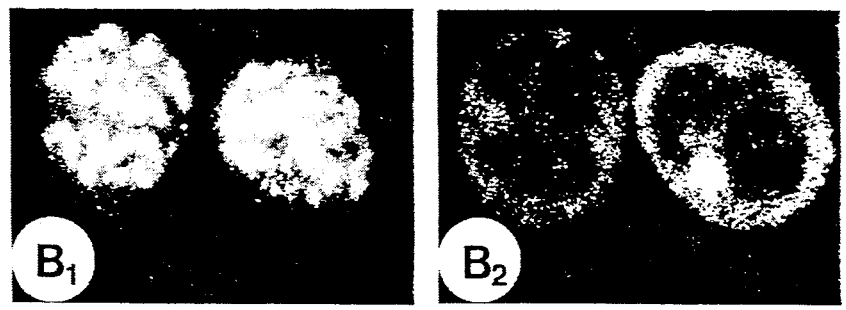
Figure 10:
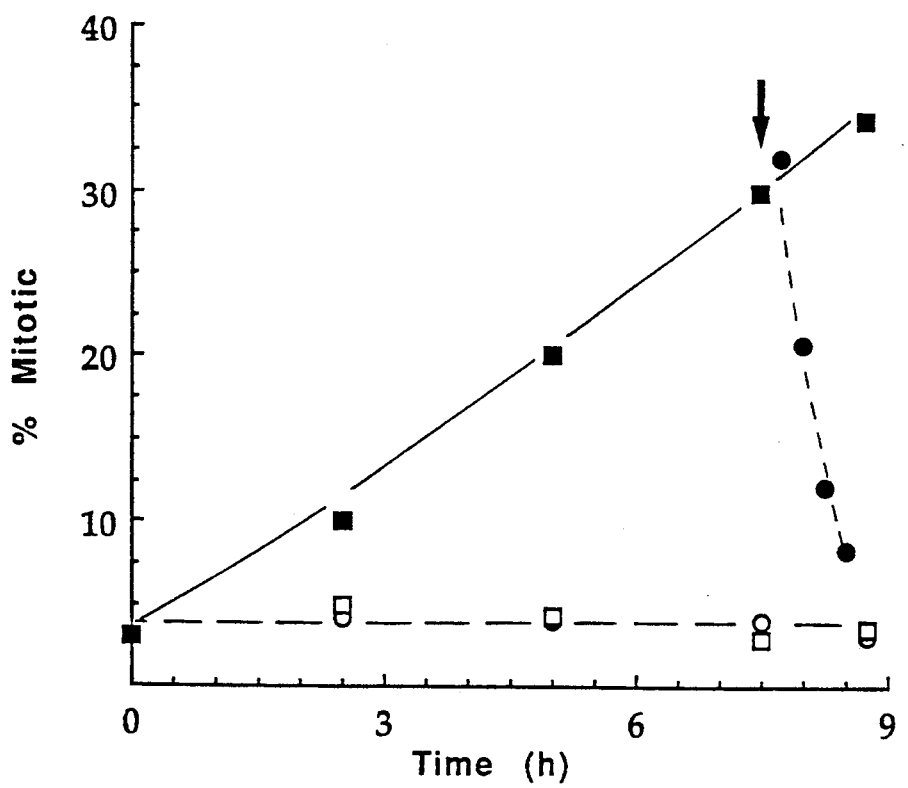
FIG. 10 shows 2-AP-induced reversion of nocodazole-blocked mitotic cells to interphase.

If nocodazole-blocked cells are exposed to 2-AP without first releasing them from nocodazole, it is evident that 2-AP induces mitotic exit signals that overcome the mitotic arrest (FIGS. 9 and 10). Prior to addition of 2-AP, nocodazole-treated cells, blocked in mitosis, display a typical array of condensed chromosomes when stained with propidium iodide (FIG. $9B_1$). When counterstained with anti-lamin B antibody, there is only a dispersed cytoplasmic stain in these cells (FIG. $9B_2$). Within 30 minutes of addition of 2-AP to these cells, still in nocodazole, their chromatin has decondensed (data not shown). After 60 minutes of 2-AP treatment, nucleoli are evident by propidium iodide (FIG. $9A_1$) and lamin B has reformed around the nucleus (FIG. $9A_2$), despite the continuous presence of nocodazole. As shown here (FIG. $9A_2$), lamin B often occurs transiently as disconnected cytoplasmic "sheets" during reentry into interphase.

Referring to FIG. 9 is more detail, nuclear reformation following the addition of 2-AP to nocodazole-blocked cells is shown. Propidium iodide staining of DNA is shown in the left column, and indirect immunofluorescent staining of lamin B is shown in the right column. The addition of 2-AP to mitotic cells in the continued presence of nocodazole induces the reformation of nuclei which are bordered by lamin B ($A_1$, $A_2$). In nocodazole-blocked cells treated with 2-AP, lamin B reassembles not only at the periphery of the nucleus, but also frequently in the cytoplasm independently of chromatin, as seen here. Otherwise untreated cells blocked in mitosis by nocodazole typically have clustered chromosomes and a dispersed lamin B stain ($B_1$, $B_2$).

A quantitative analysis of a cell population blocked with nocodazole, then additionally exposed to 2-AP shows that 2-AP rapidly causes a reversion of the cells in mitotic arrest to an interphase state (FIG. 10). We have made this analysis, scoring for either decondensed chromatin or for deposition of a lamin B border around nuclei, with comparable results. A careful examination of these nocodazole-treated cells with reconstituted nuclei reveals that they are truly in interphase, and can complete another round of DNA replication without having segregated their chromatin (data not shown). We conclude the 2-AP not only prevents chromosome condensation and function in mitosis, but also actively reverses mitotic arrest.

Referring to FIG. 10 in more detail, 2-AP -induced reversion of nocodazole-blocked mitotic cells to interphase is shown. The mitotic index of a population of cells increases in the continuous presence of nocodazole (solid squares). When 10 mM 2-AP is added to cells in the continued presence of nocodazole (arrow), the mitotic index of this population drops precipitously (solid circles). Cells were judged to be in mitosis by the absence of nuclear lamina (determined with anti-lamin B antibodies); and by the presence of discrete chromosomes, or the absence of nucleoli, both as assayed by propidium iodide staining. Control cell populations were treated continuously with 10 mM 2-AP (open squares), or were untreated except for exposure to DMSO and the HEPES used for drug treatment (open circles).

Discussion

The control of the onset of mitosis involves activation of p34$^{cdc2}$ kinase (Murray and Kirscher, 1989; Nurse, 1990; Draetta, 1990) which in turn appears to act as a master switch inducing downstream mechanisms that complete the mitotic process (Dunphy and Newport, 1988). In prophase, a number of events occur coordinately, including dissolution of nuclear structures such as lamins and nucleoli, condensation of chromosomes, separation of centrosomes, induction of kinetochore elements on chromosomes, disassembly of the cytoskeletal systems, and reassembly of microtubules into a bipolar spindle.

We have demonstrated here that the presence of 2-aminopurine (2-AP) causes cells to proceed through an aberrant partial mitosis. Partial mitosis is characterized by the transient expression of a bipolar mitotic spindle, but a failure of chromatin to form functioning chromosomes and of the cells to proceed through the recognizable mitotic phases of chromatin separation. All other morphological events associated with mitotic entry that we have examined occur normally. These include disassembly of lamin B and of the nucleolus, as well as disassembly of interphase actin cables (data not shown). Some M-phase-specific events therefore occur normally while others are aborted.

It has been shown that 2-AP is a protein kinase inhibitor (Farrell et al. 1977; Mahadevan et al. 1990), and that the inhibitory effect of 2-AP on kinase activity in vivo is quite selective. When interphase mammalian cells are exposed to 2-AP, phosphorylation is altered in a very restricted subset of proteins (Mahadevan 1990). In this context, it does not appear that partial mitosis results from inhibition of p34$^{cdc2}$ kinase itself, since mitotic entry appears to occur normally, with the exception of chromosome condensation. The selectivity of 2-AP inhibition is also indicated by the failure of 2-AP to visibly alter mitotic phosphorylation detected by MPM-2 antibodies. We therefore propose that 2-AP selectively inhibits a protein kinase activated by p34$^{cdc2}$ during mitosis.

While we have not yet identified a particular protein kinase inhibited by 2-AP in mitosis, it is reasonable to postulate that there are protein kinases with activity downstream of p34$^{cdc2}$. Other protein kinases with increased activity during mitosis have been identified in echinoderm oocytes (Pelech et al. 1988), and in mammalian cells (Chackalaparampil and Shalloway, 1988; Liu et al. 1990). Microinjection of antibodies to cyclic AMP-dependent protein kinase type II and a specific inhibitor of this kinase (Browne et al. 1987) has yielded evidence that a kinase other than p34$^{cdc2}$ is involved in progression through mitosis. There is a possibility that p34$^{cdc2}$ activates a cascade of downstream protein kinases during mitosis, as suggested by Dunphy and Newport (1988). This possibility is supported by the p34$^{cdc2}$-dependent phosphorylation of the c-src and c-abl kinases in vitro at the same sites modified in vivo (Shenoy et al. 1989; Morgan et al. 1989; Kipreos and Wang, 1990), as well as phosphorylation and activation of casein kinase II by p34$^{cdc2}$ in vitro (Mulner-Lorillon et al. 1990). As further support, Gotoh et al. (1991) have recently demonstrated that MAP2 kinase activity is directly linked to the mitosis-specific display of microtubules.

Alternative but less likely explanations for the induction of partial mitosis include the possibility that 2-AP induces a partial inhibition of p34$^{cdc2}$ itself, and that events relating to chromosome behavior have a higher threshold of activation by the kinase. It is also possible that 2-AP, as an adenine analogue, may cause partial mitosis by interfering with an ATP function unrelated to protein kinase activity.

Mitotic spindle formation in 2-AP: Among cells treated with 2-AP, those in partial mitosis generated a bipolar mitotic spindle independent of chromosome condensation. The creation of a mitotic spindle requires that signals for mitotic initiation dissolve the interphase microtubule network, that centrosomes separate to the bipolar configuration, and that microtubules emanating from each of the poles interdigitate and bundle in an antiparallel manner to form the bipolar spindle morphology.

The 2-AP-treated cells provide evidence that the spindle does not require discrete chromosomes in order to generate or maintain a bipolar morphology. This suggests that chromosomes are not requisite to engage the two half spindles or to keep them linked in their zone of overlap. The typical bipolar spindle in a 2-AP-treated cell is relatively thin compared to the more barrel-shaped spindles of control cells (see FIG. 2). This apparent paucity of microtubules between the spindle poles may arise from the fact that the entire class of kinetochore-to-pole microtubules is lacking, and only interpolar microtubules survive. This observation suggests that there are two means of stabilizing spindle microtubules against inherent instability (Mitchison and Kirschner, 1984), thus ensuring their survival. Microtubules may be stabilized either by kinetochore capture (Mitchison and Kirschner, 1985; Hayden et al. 1990), or by antiparallel interactions with polymers arising from the other half spindle (Sawin and Mitchison, 1991).

Activation of mitosis-specific microtubule arrays assembling from centrosomes in vitro has been shown to be derived, directly or indirectly, from p34$^{cdc2}$ kinase activity (Verde et al. 1990). It may be significant in this regard that p34$^{cdc2}$ becomes associated with the centrosome in late G$_2$ and remains concentrated at the centrosome through most of mitosis (Riabowol et al. 1989; Bailly et al. 1989). More recently, the mitosis-specific display of microtubules has been linked directly to MAP2 kinase activity (Gotoh et al. 1991). It appears, from our results, that these kinase activities are not appreciably affected by 2-AP treatment of cells.

Interaction of the spindle with the nucleus and with chromosomes: The bipolar spindle coexists with a structurally integral nuclear body in 2-AP-treated cells. The interaction of these two structures results in a curious phenomenon. The spindle microtubules appear to mold, deform or pierce the nuclear body. In order to generate a bipolar spindle with a spindle pole on either side of the nuclear body, the spindle poles must have separated. In doing so, their associated microtubules appear to have generated the requisite force to displace that part of the nuclear body that lay in the path of the growing spindle.

The fact that the nuclear body is deformable in 2-AP mitosis may relate to the observed loss of lamin B from the nuclear periphery in these cells. Lamin B is phosphorylated in mitotic cells by p34$^{cdc2}$, and this phosphorylation seems intimately tied to lamin disassembly (Peter et al. 1990b). Lamin B is important to the maintenance of interphase nuclear morphology. It has recently been shown in some hematopoietic cells that lamin B alone, in the absence of lamins A and C, is sufficient to form a functional nuclear lamina (Guilly et al. 1987b; Rober et al. 1990). Having exited partial mitosis, the nuclei of 2-AP-treated cells retain their mitotic deformation. It is possible that the reassembled lamins will lock in whatever shape change is imposed on the mitotic nucleus when the cell reverts to interphase.

It is not uncommon that nuclei become deformed in a characteristic manner in various cells, and the deformation is sometimes related to association with microtubules at the nuclear surface. The nucleus of the spermatocyte serves as an example (McIntosh and Porter, 1967; Doucher and Bennett, 1974). The presence of a lobed nucleus, cupped around a centrosome, is characteristic of neutrophils and monocytes (Murphy, 1976). These may represent examples in nature of transient alterations in the state of phosphorylation of lamins, allowing for microtubule-dependent molding of the nuclear exterior.

Although there is no meaningful movement of chromatin in 2-AP-treated cells, centromeres are often seen to aggregate at the periphery of the spindle. Some interaction of centromeres with the spindle is therefore possible. This may perhaps be related to the recently observed prometaphase motility of chromosomes through lateral associations of kinetochores with spindle microtubules (Rieder and Alexander, 1990). It will be of interest to determine if chromatin in 2-AP-treated mitotic cells has generated a morphologically distinct kinetochore, and has incorporated the microtubule motor protein, cytoplasmic dynein (Paschal et al. 1987), which has been reported to be present on prometaphase centromeres (Pfarr et al. 1990; Steuer et al. 1990).

Recently, we have carefully examined mitosis in BHK cells treated for only 3 hours in 2-AP (data not shown). After such relatively brief exposure to 2-AP a substantial fraction of mitotic cells contain condensed chromosomes. These chromosomes fail to engage in the spindle, and we observe no metaphase, anaphase or telophase mitotic figures. The condensation of chromosomes observed in some cells at early times suggests that the failure of chromatin condensation may result from incorporation of 2-AP into DNA during S-phase (Caras et al. 1982; Schaff et al. 1990; Speit et al. 1990). Partial mitosis as a result of 2-AP may therefore more properly be defined as the failure to form chromosomes that associate meaningfully with the spindle in mitosis, rather than as the failure of chromatin to condense into chromosomes.

We have also examined the fate of cells released from nocodazole block into 2-AP. In nocodazole-induced mitotic arrest the nucleus has dissolved and chromosomes are condensed. In this case, when the signal for chromosomal condensation has preceded 2-AP addition, the chromosomes remain condensed for at least 20 minutes. In some cells a bipolar spindle forms during nocodazole recovery and coexists with condensed chromosomes. In these cells the chromosomes exhibit little capacity to become engaged in the mitotic spindle other than by lateral association, and are never observed in typical metaphase or anaphase configurations.

Chromosomes are often arranged in a "figure of 8," surrounding the bipolar spindle at its margin. As with nuclear bodies, one frequently finds centromeres proximal to the spindle margin. As these chromosomes have apparently lost their capacity to function in the mitotic spindle, they should prove to be an interesting model system for the in vitro reestablishment of kinetochore function by addback of mitotic factors.

Mitosis exit signals and 2-AP: The mitotic index of a cell population is not altered measurably by 2-AP. There is thus no evidence that 2-AP-treated cells are hindered in transiting mitosis despite the lack of the distinct mitotic phases that may act as "checkpoints" in mitotic progression (Hartwell and Weinert, 1989).

By criteria of chromatin and centromere distribution with respect to the spindle, 2-AP-treated cells never enter metaphase or anaphase. These cells also never exhibit furrowing indicative of telophase, and probably also exit mitosis without induction of cleavage signals. Further evidence that 2-AP-treated cells do not undergo cleavage comes from the fact that these cells do not display the midbodies evident in control cells by tubulin antibody staining (data not shown).

Cells in 2-AP not only transit through mitosis without a requirement for completing downstream mitotic events, they can, in fact, overcome mitotic arrest. Cells blocked in nocodazole will remain in mitotic arrest for an indefinite period of time, but the addition of 2-AP to nocodazole-arrested cells induces a rapid reversal of the arrested state, as evidenced by reformation of nuclei with lamin borders in the continued presence of nocodazole.

The induction of cell cycle progression in M-phase-arrested cells is analogous to the effect of 2-AP and other purine analogues on S-phase-arrested cells. Cells can be arrested indefinitely in S-phase by drugs such as hydroxyurea (Tobey, 1973), but the addition of purine analogues to these cells induces escape from S-phase, leading to chromosome condensation (Schlegel and Pardee, 1986; Schlegel et al. 1990; Downes et al. 1990). Among the purine analogues with an effect on S-phase, we have found 2-AP and 6-dimethylaminopurine, but not caffeine, are successful in overcoming nocodazole-induced mitotic arrest (data now shown).

It has been shown that 6-dimethylaminopurine causes rapid decondensation of chromosomes at metaphase I of meiosis in oocytes of the mollusc Patella vulgata and in mouse oocytes (Neant and Guerrier, 1988; Rime et al. 1989). This decondensation is accompanied by substantial inhibition of protein phosphorylation specific to meiosis. We have found, in BHK cells, that 6-dimethylaminopurine causes partial mitosis events similar to those observed with 2-AP (data now shown). It is therefore possible, in view of our results, that 6-dimethylaminopurine induces a partial meiosis in the oocyte system.

Conclusions

The results reported here in BHK cells have been reproduced in HeLa (data not shown). We expect that the 2-AP induction of partial mitosis will prove to be widespread in occurrence. The ability to block certain mitotic events while other events proceed normally should prove valuable for biochemical dissection of the control of specific mitotic phenomena induced by p34$^{cdc2}$. Assuming that the mitotic effects of 2-AP are primarily due to its action as a specific kinase inhibitor (Farrell et al. 1977; Mahadevan et al. 1990), the drug may allow identification of specific downstream mitotic kinases and their substrates. Further, our observations on 2-AP treatment of cells raise questions as to the interaction and interdependency of various events that occur in succession in a normal mitosis, and should permit the biochemical analysis of the molecular nature of mitotic checkpoints (Hartwell and Weinert, 1989) in mammalian cells.

SECOND SERIES OF EXAMPLES

BHK cells blocked at any of several arrest points in the cell cycle override their arrest and proceed in the cycle when exposed simultaneously to the protein kinase inhibitor 2-aminopurine (2-AP). For cells arrested at various points in interphase, 2-AP-induced cell cycle progression is made evident by arrival of the drug-treated cell population in mitosis. Cells that have escaped mimosine $G_1$ arrest, or from hydroxyurea or aphidicolin S-phase arrest, or from VM-26-induced $G_2$ arrest subsequently have all the hallmarks of mitosis such as a mitotic microtubule array, nuclear envelope breakdown, and chromatin condensation. In a synchronous population, the time course of arrival in mitosis, and its duration, in 2-AP treated cells that have escaped cell cycle blocks is indistinguishable from control cells. Cells arrested in mitosis by nocodazole or taxol quickly escape mitotic arrest and enter interphase when exposed to 2-AP. 2-AP by itself does not influence the timing of cell cycle progression. We conclude that 2-AP acts to override checkpoints in every phase of the cell cycle, perhaps by inhibiting a protein kinase responsible for control of multiple cell cycle checkpoints.

Materials and Methods

Cell culture and synchronization: Baby hamster kidney (BHK) cells were grown as monolayers in Dulbecco's Modified Eagle's Medium (Gibco Laboratories), supplemented with 10% defined fetal bovine serum (Hyclone Laboratories), and were maintained in a humid incubator at 37° C. in a 5% $CO_2$ environment.

Drug treatment: 2-Aminopurine was obtained from Sigma Chemical Co. as a nitrate salt. A stock of 100 mM 2-AP was kept frozen in 100 mM Hepes buffer at pH 7.2. In experiments where 2-AP was applied, control cells received identical final concentrations (10 mM) of Hepes buffer. Aphidicolin, hydroxyurea, and mimosine were obtained from Sigma and used at final concentrations of 5 $\mu$M, 2 mM, and 200 $\mu$M, respectively. VM-26 (Bristol-Meyers) was used at 0.45–0.50 $\mu$g/ml. For examination of the response of mitotic blocks to 2-AP treatment, nocodazole was used at 0.06 $\mu$g/ml and taxol (the gift of M. Suffness, NIH) at 5 $\mu$M.

Determination of mitotic index: For testing mitotic blockage with nocodazole and taxol, cells were grown a minimum of 16 hours on polylysinecoated glass coverslips before drug treatment. Cells were fixed at intervals, stained with antibodies to detect lamin B, and counterstained with propidium iodide to assay chromosome condensation. To test cell cycle blocks in interphase, cells were synchronized in mitosis by addition of nocodazole (Sigma Chemical Co.) to a final concentration of 0.05 μg/ml from a 1 mg/ml stock in dimethylsulfoxide. After 12 hours arrest, the mitotic subpopulation was isolated by shakeoff from the culture plate. After applying cell cycle blocking drugs and/or 2-AP, cells were fixed at intervals, prepared for indirect immunofluorescence with anti-tubulin antibodies, and counterstained with propidium iodide. All data timepoints represent averages of three counts of greater than 150 cells each. Standard deviation was never more than 1.5% on the ordinate scale.

Immunofluorescence microscopy: Cells were fixed for 20 minutes with 2% paraformaldehyde in PBS (136 mM NaCl, 2 mM KCl, 10.6 mM $Na_2PO_4$, 1.5 mM $KH_2PO_4$, pH 7.4) at 37° C. Cells were then washed with PBS, permeabilized 3 minutes with 0.2% Triton X-100 in PBS, and washed 3 times with PBS. Primary and secondary antibodies were applied in PBS, also containing 3% bovine serum albumin, 0.05% Tween-20, and 0.1% sodium azide. Incubation with primary antibodies (60 minutes in a humid chamber at 37° C.) was followed by three washes with PBS as above. Primary antibodies included mouse anti-$\beta$-tubulin antibody (Eastacres Biologicals, Southbridge, Mass.), diluted 25-fold for use, and anti-lamin B human autoimmune serum (Guilly et al., 1987), a gift from Dr. J-C Courvalin, diluted 200-fold for use. Coverslips were then exposed to secondary antibodies for 30 minutes at 37° C. in a humid chamber. Secondary antibodies included FITC-conjugated affinity-purified goat anti-mouse and anti-human antibodies, applied at 8.5 μg/ml. Secondary antibodies were from Tago, Inc. (Burlingame, Calif.). Cover slips were then washed twice with PBS, both before and after 5 minutes incubation with propidium iodide (1 μg/ml in PBS).

For microscopy, coverslips were mounted with 25 mg/ml of 1,4-diazabicyclo-(2.2.2)octane (Kodak) in 90% glycerol/PBS, pH 8.6 (Johnson et al., 1982), and samples were recorded using a MRC-500 Laser Scanning Confocal apparatus (Bio-Rad Microscience) attached to a Nikon Optiphot microscope (Nikon Inc.).

Flow cytometric analysis of DNA content: Samples were fixed 30 minutes on ice with 70% ethanol/1X PBS (136 mM NaCl, 2 mM KCl, 10.6 mM $Na_2HPO_4$, 1.5 mM $KH_2PO_4$, pH 7.4), and then stored at 4° C. until preparation for staining. Prior to analysis, cells were washed twice with PBS, then stained using the optimal procedure reported by Tate et al. (1983). Measurements of propidium iodide fluorescence signal were made using an Epics 753 analyzer (Coulter) on $10^4$ cells.

Results

It has been demonstrated that cells arrested in S-phase by hydroxyurea escape the S-phase block when exposed to 2-AP (Schlegel et al., 1990). Further, we have observed that BHK cells blocked in mitosis by nocodazole rapidly exit mitosis upon addition of 2-AP (see above). We have tested to determine if these effects result directly from interference with the cell cycle by 2-AP alone. For this, BHK cells were synchronized by shakeoff of the mitotic subpopulation and assayed for timing of progression through the cell cycle, by flow cytometric analysis of DNA content (FIG. 11A) and time of arrival in the subsequent mitosis (FIG. 11B), while constantly exposed to 10 mM 2-AP.

Figure 11A:
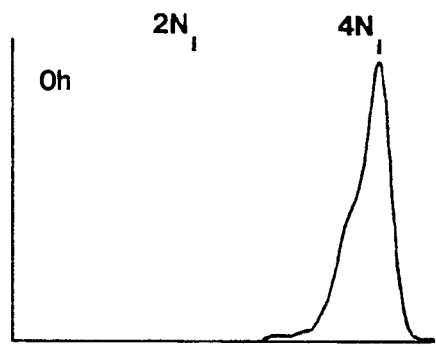
FIGS. 11A–11E shows the effect of 2-AP on the cell cycle.
Figure 11B:
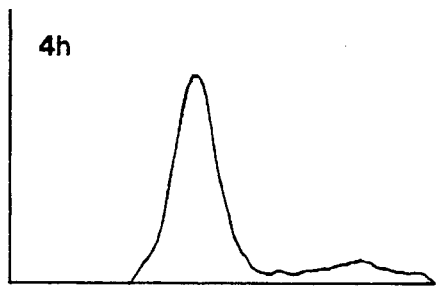
Figure 11C:
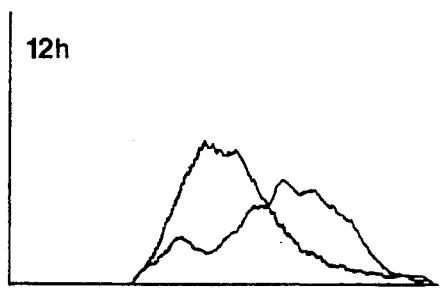
Figure 11D:
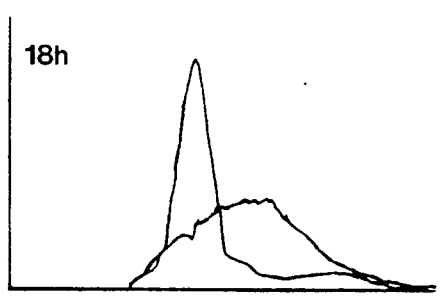
Figure 11E:
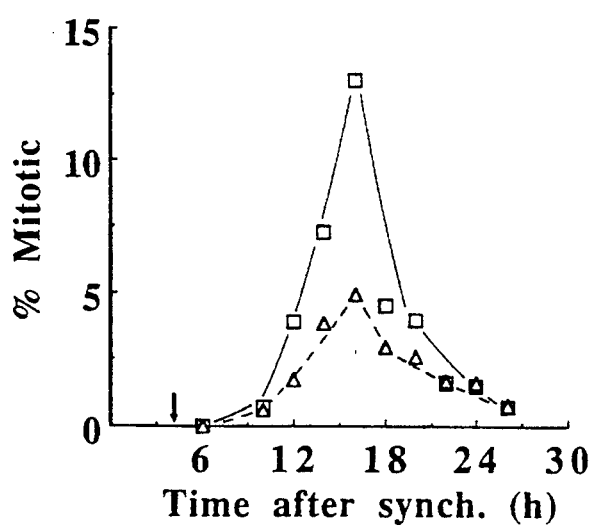

Mitotic shakeoff of nocodazole-arrested cells resulted in a starting population of mitotic cells with 4N DNA content (FIG. 11A). The drug 2-AP was applied four hours after shakeoff and recovery from nocodazole arrest, when the majority of the cells had reentered $G_1$ (FIG. 11A). S-phase appears to initiate at approximately the same time in both 2-AP treated and control cells, about 6 hours after synchronization (data not shown). Analysis of DNA content is also shown at 12 hours following synchronization, when the control cells are approaching 4N DNA content and the first mitotic cells are visualized morphologically, and also at 18 hours, when mitosis is largely completed in control cells. Treatment with 2-AP causes a marked delay in S phase, with DNA synthesis lagging behind controls at 12 hours, and remaining incomplete for the population 18 hours after synchronization (FIG. 11A). Interestingly, many of the 2-AP treated BHK cells apparently fail to complete S-phase, yet arrive in mitosis at approximately the same time as control cells (FIG. 11B). These results show there is no acceleration of the mitotic cycle in the presence of 2-AP, but suggest that cells in 2-AP do not appear to respect the requirement for completion of S-phase before proceeding to mitosis.

Referring to FIG. 11 in more detail, the effect of 2-AP on the cell cycle is shown. BHK cells were synchronized by shakeoff detachment of nocodazole-arrested mitotic cells, and cell cycle progression in the presence or absence of 10 mM 2-AP was assayed following the removal of nocodazole. 2-AP was added to the synchronized cells at 4.5 hours after shakeoff. (A) DNA content, assayed by flow cytometry, is shown of mitotic cells at shakeoff (0 hours), at the time of 2-AP addition (4.5 hours), and comparing the control population (light lines) to 2-AP-treated cells (heavy lines) at 12 hours and 18 hours after synchronization. (B) The mitotic index, determined by anti-tubulin immunofluorescence, and by propidium iodide assay of chromatin condensation, was scored over a period of 24 hours following mitotic shakeoff for 2-AP treated (triangles) and control populations (squares).

Override of $G_1$, S-phase, $G_2$, and M-phase cell cycle blocks by 2-AP: Mammalian culture cells may be blocked in the various parts of the cell cycle by specific inhibitors. Mimosine, an amino acid analogue, has been reported to block cells at a point in $G_1$ that precedes S-phase by about two hours (Lalande, 1990). Aphidicolin and hydroxyurea, inhibitors of DNA polymerase α (Ikegami et al., 1978) and ribonucleotide reductase (Moore, 1969), respectively, block cells in early S-phase. VM-26, a topoisomerase II inhibitor (Chen et al., 1984), induces a cell cycle block in $G_2$ (Misra and Roberts, 1975). Nocodazole and taxol, drugs that interfere with normal microtubule assembly behavior (Zieve et al., 1980; Schiff et al., 1980), block cells in mitosis.

As 2-AP will overcome an S-phase block (Schlegel et al., 1990), and induces nocodazole-blocked cells to exit mitosis (see above), we have tested the ability of 2-AP to override any of a variety of different cell cycle blockages specific to different stages. For each experimental test except blockage at mitosis, cells were first synchronized by shakeoff in a nocodazole-arrested mitotic state, then allowed to recover from nocodazole, and exposed to the blocking agent either in the presence or absence of 10 mM 2-AP. In each case, the cell cycle behavior of drug-treated cells was compared with the behavior of untreated control cells.

Cells were tested for their ability to overcome mimosine G$_1$ arrest in 2-AP by assaying the mitotic index at time points following drug addition. BHK cells treated with both mimosine and 2-AP exhibited the same time course and amplitude of arrival in mitosis as untreated controls (FIG. 12A), whereas cells treated with mimosine alone did not pass through mitosis (FIG. 12A). Mimosine+2-AP blocked cells did not engage in DNA replication, but remained 2N until mitosis, as assayed by FACS analysis (FIG. 12B). Mimosine-treated cells, either with or without 2-AP, also showed no intranuclear accumulation of PCNA (Takasaki et al., 1981; Bravo and MacDonald-Bravo, 1985), an S-phase marker (data not shown). Thus, entry into mitosis did not result from a simple reversal of the mimosine block. Mimosine+2-AP cells were determined to be in mitosis by the criteria of rounding, condensation of chromatin, and loss of nucleolar structures, and by the loss of the interphase microtubule array. In the place of a fully formed mitotic spindle, these cells had a single small aster adjacent to the chromatin (FIG. 12C).

Referring to FIG. 12 in more detail, 2-AP overrides mimosine dependent G$_1$ blockage. (A) Cells were synchronized in mitosis and assayed for mitotic index in the next cell cycle, as in FIG. 11. Cells were continuously exposed to 200 µM mimosine alone (circles) or to 200 µM mimosine+10 mM 2-AP (triangles). The point of drug addition is indicated by an arrow. (B) Flow cytometry analysis of cells in mimosine alone (light line) and in mimosine+2-AP (heavy line), performed on cells at the point of maximal control cell mitosis (18 hours after shakeoff). Mimosine-blocked cells are uniformly 2N. (C) Immunofluorescence image of a typical mitotic cell in mimosine+2-AP shows a small, intensely staining mitotic aster detected with anti-tubulin antibody (left), and condensed mitotic chromatin is imaged with propidium iodide (center). The merged image is also shown (right).

Similarly, BHK cells overcame S-phase arrest upon addition of 2-AP (FIG. 13). This ability to override S-phase arrest, as assayed by ability to undergo mitosis, was independent of whether the arrest was induced by hydroxyurea (FIG. 13A) or aphidicolin (FIG. 13B), which are unrelated inhibitors of DNA synthesis. Again, both the timing and amplitude of mitosis was comparable to controls (FIG. 13A). Again, both the timing and amplitude of mitosis was comparable to controls (FIGS. 13A and 13B). Cells treated with hydroxyurea+2-AP differed from mimosine+2-AP treated cells in that they typically exhibited a small bipolar spindle (FIG. 13C). This bipolar spindle was arranged either parallel (as shown) or perpendicular to the chromatin mass. Neither of these spindle arrangements occur in cells treated with 2-AP alone (see above), and the spindle is smaller than in 2-AP-treated cells. Flow cytometric analysis showed that the cells that overrode S-phase blockage did not proceed through S-phase replication, but remained 2N at the time of mitosis (data not shown).

Referring to FIG. 13 in more detail, override of hydroxyurea and aphidicolin S-phase blocks by 2-AP is shown. Cells were synchronized and assayed for mitotic behavior as in FIG. 11. The mitotic index, assayed by rearrangement of microtubules (with anti-tubulin antibody) and by chromatin condensation (with propidium iodide), is shown for treatments at 4 hours (arrow) involving hydroxyurea (A) and aphidicolin (B). For each, symbols are as follows: control cells (squares), 2 mM hydroxyurea or 5 µM aphidicolin (circles), and 2 mM hydroxyurea or 5 µM aphidicolin+10 mM 2-AP (triangles). Immunofluorescence images (C), using anti-tubulin and propidium iodide, show a mitotic cell in hydroxyurea+2-AP at 18 hours after shakeoff. This cell contains a small mitotic spindle (above), and condensed chromatin (center). A merged image (below) shows the spindle characteristically positioned adjacent to the chromatin.

Figure 14A:
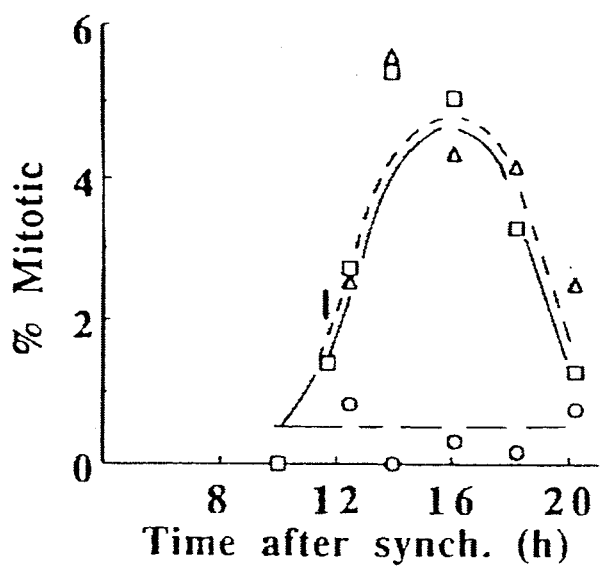
FIGS. 14A–14D shows override of VM-26-dependent $T_2$ block by 2-AP.
Figure 14B:
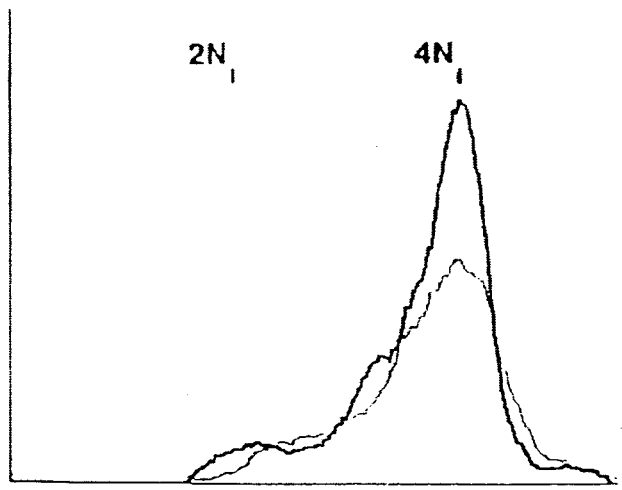
Figure 14C:
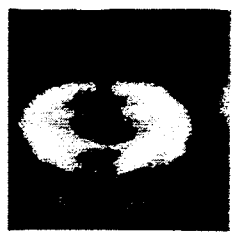
Figure 14D:
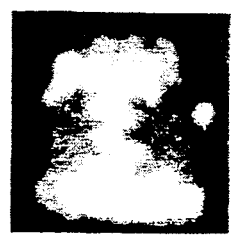

BHK cells are blocked in G$_2$ by VM-26, as determined by their failure to enter mitosis (FIG. 14A) and by FACS analysis (FIG. 14B). Simultaneous treatment with VM-26 and 2-AP causes these cells to override the G$_2$ block and enter mitosis (FIGS. 14A, 14B). The time of arrival in mitosis is the same as for untreated control cells. A full mitotic spindle forms, but chromosomes do not integrate into the spindle. Cells treated in this manner exhibit a phenomenon we have termed "partial mitosis" (see above) in that they exit mitosis without proceeding through metaphase, anaphase, or telophase. Given that VM-26 acts on topoisomerase II, a major component of the chromosome scaffold (Earnshaw et al., 1985), and is believed to prevent mitotic entry by inhibition of chromatin condensation (Charron and Hancock, 1990), it is surprising that chromatin is clearly condensed into chromosomes during partial mitosis in VM-26+2-AP (FIG. 14C).

Referring to FIG. 14 in more detail, override of VM-26 dependent G$_2$ block by 2-AP is shown. Cells were synchronized and assayed as in FIG. 11. (A) Mitotic index, determined by microscopic assay as in FIG. 11, is shown for controls (squares), and for cells exposed at 11 hours (arrow) after shakeoff to the following conditions: 0.45 µg/ml VM-26 alone (circles), or VM-26+10 mM 2-AP (triangles). (B) Cells, arrested in VM-26 at 11 hours after shakeoff, and assayed by flow cytometry (FACS) after 7 hours in VM-26 (light line), or VM-26+2-AP (heavy line), remain 4N. At this time, control cells are fully divided (see FIG. 11A). (C) Immunofluorescence microscopy, as in FIG. 12, of a typical mitotic cell in VM-26+2-AP at 18 hours post-shakeoff. Condensed chromatin (right) does not integrate into the mitotic spindle (left).

Figure 15:
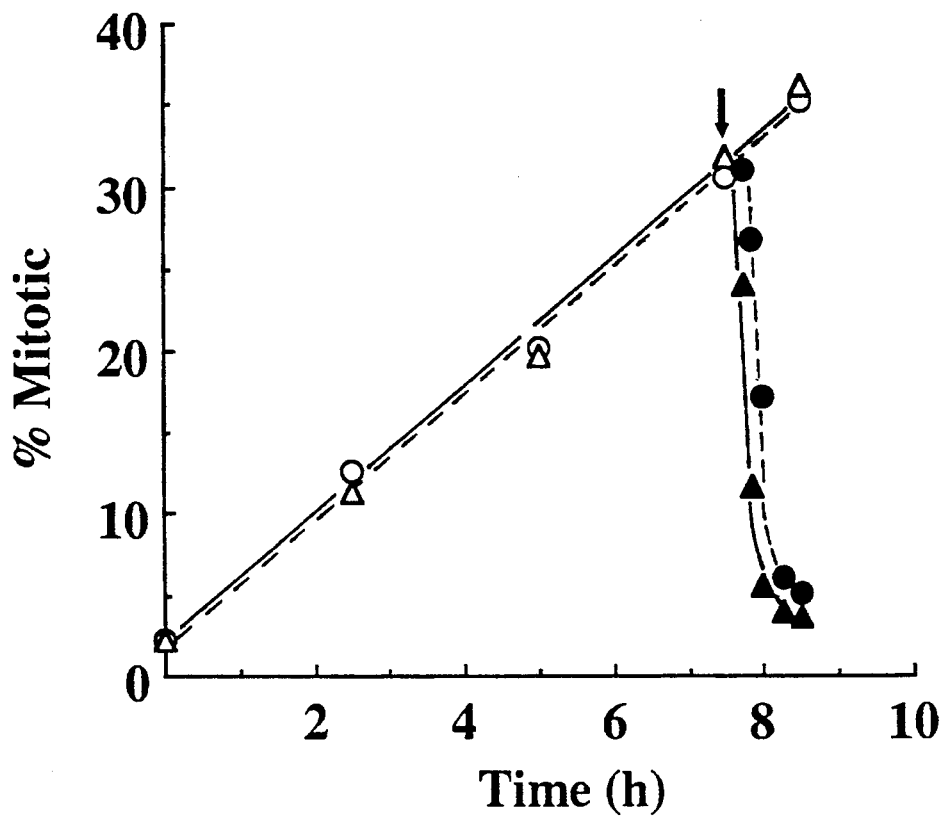
FIG. 15 shows override of mitotic block by 2-AP, independent of the microtubule assembly state.

2-AP also overrides mitotic arrest, independent of the drug used to block cells in mitosis. In the presence of either taxol or nocodazole, BHK cells arrest in mitosis (FIG. 15). Upon addition of 2-AP, these blocked cells rapidly exit mitosis (FIG. 15) without proceeding through mitotic stages. This result shows that override of the block and subsequent mitotic exit is independent of the assembly state of tubulin during blockage, as nocodazole prevents microtubule assembly (Zieve et al., 1980) and taxol locks microtubules into a fully assembled state (Schiff et al., 1980).

Referring to FIG. 15 in more detail, override of mitotic block by 2-AP, independent of the microtubule assembly state, is shown. A randomly cycling BHK cell population was treated with mitotic inhibitors. The resulting mitotic index, determined by immunofluorescence microscopy of the dispersion of lamin B, and confirmed by propidium iodide assay of chromatin condensation, shows mitotic cells accumulate with either 0.06 µg/ml nocodazole (open circles) or 5 µM taxol (open triangles), applied at time 0. Addition of 10 mM 2-AP (arrow) causes rapid exit of blocked cells from mitosis (nocodazole+2-AP, closed circles; taxol+2-AP, closed triangles).

Discussion

We have demonstrated that 2-AP acts to override every cell cycle block analyzed, regardless of the stage of the mitotic cycle in which the blockage has occurred. In every case, the drug does not release the cell from any specific blockage, but causes it to proceed aberrantly toward subsequent mitotic stages as though no block existed. By itself, 2-AP neither retards nor accelerates progress through a cell cycle toward mitosis.

Negative regulators of downstream mitotic events, called checkpoints, have been identified by genetic criteria (Hartwell and Weinert, 1989). These regulators require the completion of prerequisite events before advancement in the cell cycle. Such checkpoints occur to ensure the fidelity of chromosomal segregation to daughter cells (Hartwell and Weinert, 1989).

Checkpoints have been examined in mammalian cells using treatments that inhibit DNA replication and induce DNA repair (Lau and Pardee, 1982; Schlegel and Pardee, 1986; Musk et al., 1988). Steinman et al. (1991) have demonstrated that 2-AP, as well as 6-dimethylaminopurine and caffeine, override these checkpoints. In the present disclosure, we have examined checkpoints, unrelated to DNA replication and repair, that govern progression throughout the cell cycle. The fact that 2-AP can override every checkpoint assayed suggests that there is a commonality in the mechanism of checkpoint arrest at different points in the cell cycle.

In addition to overriding checkpoints in the cell cycle created by drug blockage, 2-AP also appears to cause a failure of normal checkpoint controls. Thus, in the presence of 2-AP alone, the rate of DNA replication appears to be somewhat retarded relative to that in control cells, but 2-AP treated cells exit S phase and arrive at mitosis at the appropriate time regardless of incomplete DNA replication in the population. Further, as we discuss above, BHK cells exit mitosis in 2-AP without respecting the checkpoint (Rieder and Alexander, 1990) that requires the alignment of their chromosomes in a metaphase plate.

It is of obvious interest now to determine whether, as the data suggest, 2-AP acts always on the same effector at different points in the cell cycle. It may be imagined that the same enzyme acts as a negative regulator at each of several points in the cell cycle, blocking progress until certain conditions are met, and that 2-AP inhibits this enzyme's activity and therefore causes the cell to bypass checkpoint controls. The purine analogue is known to be a highly selective inhibitor of protein kinase activity in vivo (Mahadevan et al., 1990), as the drug down-regulates the phosphorylation of a very limited subset of the phosphoproteins in the cell. The identity of the phosphorylated substrates and of the protein kinase(s) inhibited by 2-AP in vivo are presently unknown.

At the molecular level, control of progression in the cell cycle is best understood at the point of entry into mitosis. It is evident that, at this point, the phosphorylation state of p34$^{cdc2}$ and its association with cyclin B are critical to the induction of a variety of mitosis-specific events by p34$^{cdc2}$ kinase activity (Murray et al., 1989; Nurse, 1990). If p34$^{cdc2}$ is phosphorylated on tyr-15, it must be dephosphorylated in order for entry into mitosis to ensue, in a process that is dependent on cdc25 (Gould et al., 1989). Okadaic acid, a potent inhibitor of protein phosphatases 1 and 2A (Bialojan and Takai, 1988), has been shown to induce premature entry into mitosis by dephosphorylation of p34$^{cdc2}$, and promotes exit from mitosis by degradation of cyclin B (Yamashita et al., 1990). Okadaic acid appears to act directly on p34$^{cdc2}$ rather than on checkpoint controls, since 0.5 μM okadaic acid induces a rapid premature entry into mitosis of unblocked mid-S-phase cells (Yamashita et al., 1990).

In yeast, wee1 and mik1 are implicated in the inhibitory regulation of p34$^{cdc2}$, probably by direct or indirect control of the phosphorylation state of tyr-15 (Lundgren et al., 1991). Both wee1 and mik1 are protein kinases which appear to act on cdc2 (Lundgren et al., 1991), and wee1 has the reported unusual property of being a serine/tyrosine protein kinase (Featherstone and Russell, 1991). In mitosis, wee1 mik1 double mutants behave in a manner similar to mammalian cells exposed to 2-AP. As observed in BHK cells (see above), the yeast double mutants undergo an aberrant mitosis at restrictive temperature, characterized by abnormal patterns of chromosome segregation and septum formation (Lundgren et al., 1991). Of greatest importance, the wee1 mik1 double mutant, combined with various cdc cell cycle arrest mutants, does not respect checkpoints in G1, S phase, or G2 at restrictive temperatures (Lundgren et al., 1991).

Since 2-AP overrides checkpoints throughout interphase, as well as at mitosis, it is a reasonable possibility that 2-AP may act to inhibit the wee1 (Igarashi et al., 1991) or mik1 homologue in mammalian cells. The two protein kinases share substantial sequence homology, and both contain ATP binding sequences that are unlike the common motif shared by other protein kinases (Lundgren et al., 1991), and may therefore be specifically inhibitable by particular purine analogues.

The pim1 gene encodes an RCC1 homologue in yeast (Matsumoto and Beach, 1991). Mutation of RCC1 in mammalian cells, or of pim1 in yeast, leads to premature chromosome condensation in the absence of DNA replication. This suggests that checkpoint mechanisms, like p34$^{cdc2}$ regulation of the cell cycle, are conserved over diverse phyla. As observed for 2-AP-treated BHK cells, both pim1 (Matsumoto and Beach, 1991) and wee1 mik1 double mutants (Lundgren et al., 1991) overcome checkpoints throughout interphase. These observations further suggest conservation of checkpoint mechanisms through evolution.

Dissociation of cell cycle progression from stage-specific events is revealed here by the combined treatment of BHK cells with stage-specific blocks and 2-AP. For instance, the mimosine G$_1$ block interferes with either the induction of S phase or with the replication process, but signals nonetheless induce mitosis in these cells at the appropriate time. There also appears to be a stage-specific maturation of the mitotic microtubule organizing centers: G$_1$ blocked cells, treated with 2-AP, typically transit mitosis with a single small aster; S-phase blocked cells exhibit a small "safety pin" spindle; whereas G$_2$ blocked cells exhibit an apparently mature spindle.

Previous data from in vitro models and from VM-26 treatment of intact cells have strongly suggested that topoisomerase II is requisite for chromosome condensation (Charron et al., 1990; Wood et al., 1990). Surprisingly, we find condensed chromosomes in mitotic cells treated with VM-26 and 2-AP. Our results therefore strongly suggest that VM-26 does not directly inhibit topoisomerase II-dependent chromosome condensation. It thus appears that the topoisomerase II activity required for exit from $G_2$ involves a checkpoint independent of the capacity for chromosome condensation.

It has been noted that override of checkpoints in yeast by wee1 mik1 double mutants results in a lethal M phase (Lundgren et al., 1991). Similarly, it is evident from our observations reported herein that override of any of several cell cycle blocks by 2-AP is ultimately lethal to the cell (data not shown). Several drugs that arrest cells at specific stages of their cycle, such as VM-26, taxol, and vinblastine, have been used with success in tumor therapy. As override of cell cycle arrest is lethal, our results indicate that a combination of VM-26 or taxol therapy with a purine analogue such as 2-AP represents a highly effective "binary" treatment of sensitive tumors.

While the preferred embodiments of the invention has been illustrated and described, it will be appreciated that various changes can be made therein without departing from the spirit and scope of the invention.

Citations

Bailly, E., et al. 1989. p34$^{cdc2}$ is located in both nucleus and cytoplasm—part is centrosomally associated at G2/M and enters vesicles at anaphase. EMBO J. 8:3985-3995.

Belenguer, P., et al. 1990. Mitosis-specific phosphorylation of nucleolin by p34$^{cdc2}$ kinase. Mol. Cell. Biol. 10:3607-3618.

Bialojan, C. & Takai, A. (1988), Inhibitory effect of a marine-sponge toxin, okadaic acid, on protein phosphatases, *Biochemical Journal*, 256:283-290.

Blow, J. J. & Nurse, P. (1990), A cdc2-like protein is involved in the initiation of DNA replication in Xenopus egg extracts, *Cell*, 62:855-862.

Bravo, R. & MacDonald-Bravo, H. (1985), EMBO J., 4:655-661.

Browne, C. L., et al. 1987. Effect of inhibition of the catalytic activity of cyclic AMP-dependent protein kinase on mitosis in PtK cells. Cell Motil. and the Cytoskel. 7:248-257.

Caras, I. W., et al. 1982. Mechanism of 2-Aminopurine mutagenesis in mouse T-lymphosarcoma cells. Molec. Cell Biol. 2:1096-1103.

Chackalaparampil, I., and Shalloway, D. 1988. Altered phosphorylation and activation of PP60$^{c\text{-}src}$ during fibroblast mitosis. Cell 52:801-810.

Charron, M. & Hancock, R. (1990), *Biochemistry*, 29:9531-9537.

Chen, G. L., et al. (1984), Nonintercalative antitumor drugs interfere with the breakage-reunion reaction of mammalian topoisomerase II, *J. Biological Chem.*, 259:13560-13566.

Chou, Y. H., et al. 1990. Intermediate filament reorganization is mediated by p34$^{cdc2}$ phosphorylation of vimentin. Cell 62:1063-1071.

Dasso, M. and Newport, J. W. (1990), Completion of DNA replication is monitored by a feedback system that controls the initiation of mitosis in in vitro studies in Xenopus, *Cell*, 61:811-823.

Davis, F. M., et al. 1983. Monoclonal antibodies to mitotic cells. Proc. Natl. Acad. Sci. USA 80:2926-2930.

Docher, G. B., and Bennett, D. 1974. Abnormal microtubular systems in mouse spermatids associated with a mutant gene at the T-locus. J. Embryol. and Exp. Morphol. 32:749-762.

Downes, C. S., et al. 1990. Caffeine overcomes a restriction point associated with DNA replication, but does not accelerate mitosis. J. Cell Biol. 110:1855-1859.

Draetta, G. (1990), Cell cycle control in eukaryotes: molecular mechanisms of cdc2 activation, *Trends in Biochem. Sci.*, 15:378-383.

Dunphy, W. G., and Newport, J. W. 1988. Mitosis-inducing factors are present in a latent form during interphase in the Xenopus embryo. J. Cell Biol. 106:2047-2056.

D'Urso, G., et al. (1990), Cell cycle control of DNA regulation by a homologue from human cells of the p34$^{cdc2}$ protein kinase, *Science*, 250:786-791.

Earnshaw, W. C., et al. (1985), Topoisomerase is a structural component of mitotic chromosome scaffolds, *J. Cell Biology*, 100:1706-1715.

Fang, F. & Newport, J. W. (1991), Evidence that the G1-S and G2-M transitions are controlled by different cdc2 proteins in higher eukaryotes, *Cell*, 66:731-742.

Farrell, P. J., et al. (1977), Phosphorylation of initiation factor eIF-2 and the control of protein synthesis, *Cell*, 11:187-200.

Featherstone, C. & Russell, P. (1991), Fission yeast p107wee1 mitotic inhibitor is a tyrosine/serine kinase, *Nature*, 349:808-811.

Gotoh, Y., et al. 1991. In vitro effects on microtubule dynamics of purified Xenopus M phase-activated MAP kinase. Nature 349:251-254.

Gould, K. L. & Nurse, P. (1989), Tyrosine phosphorylation of the fission yeast cdc2+protein kinase regulates entry into mitosis, *Nature*, 342:39-45.

Guilly, M. N., et al. (1987), Autoantibodies to nuclear lamin B in a patient with thrombopenia, *Eur. J. Cell*, 43:266-272.

Guilly, M. N., et al. 1987b. A human T lymphoblastic cell line lacks lamins A and C. EMBO J. 6:3795-3799.

Hartwell, L. H. & Weinert, T. A. (1989), Checkpoints: controls that ensure the order of cell cycle events, *Science*, 246:629-634.

Hayden, J. H., et al. 1990. Kinetochores capture astral microtubules during chromosome attachment to the mitotic spindle: direct visualization in live newt lung cells. J. Cell Biol. 111:1039-1045.

Hoyt, M. A., Totis, L. & Roberts, B. T. (1991), Cell 66, 507-517.

Ikegami, S., et al. (1978), Aphidicolin prevents mitotic cell division by interfering with the activity of DNA polymerase a, *Nature*, 275:458-460.

Igarashi, M., et al. (1991), Wee1$^+$-like gene in human cells, *Nature*, 353:80-83.

Johnson, et al. 1982. Fading of immunofluorescence during microscopy: a study of the phenomenon and its remedy. J. Immunol. Methods 55:231-242.

Kipreos, E. T., and Wang, J. Y. J. 1990. Differential phosphorylation of c-abl in cell cycle determined by cdc2 kinase and phosphatase activity. Science 248:217-220.

Lalande, M. (1990), A reversible arrest point in the late G1 phase of the mammalian cell cycle, *Experimental Cell Research*, 186:332-339.

Langan, T. A., et al. 1989. Mammalian growth-associated H1 histone kinase: a homolog of cdc2+/cdc28 protein kinases controlling mitotic entry in yeast and frog cells. Mol. and Cell. Biol. 9:3860-3868.

Lau, C. C. & Pardee, A. B. (1982), Mechanism by which caffeine potentiates lethality of nitrogen mustard, *Proc. Natl. Acad. Sci. U.S.A.*, 79:2942–2946.

Li, R. & Murray, A. W. (1991). Cell 66, 519–531.

Liu, J., et al. 1990. Cell cycle-mediated structural and functional alteration of p85$^{gag\text{-}mos}$ protein kinase activity. Oncogene 5:171–178.

Lundgren, K., et al. (1991), Mik1 and wee1 cooperate in the inhibitory tyrosine phosphorylation of cdc2, *Cell*, 64:1111–1122.

Mahadevan, L. C., et al. (1990), 2-aminopurine abolishes EGF- and TPA-stimulated pp33 phosphorylation and c-fos induction without affecting the activation of protein kinase C, *Oncogene*, 5:327–335.

Matsumoto, T. & Beach, D. (1991), Premature initiation of mitosis in yeast lacking RCC1 or an interacting GTPase, *Cell* 66:347–360.

McIntosh, J. R., and Porter, K. R. 1967. Microtubules in the spermatid of the domestic fowl. J. Cell Biol. 35:153–173.

Minshull, J., et al. (1989), The role of cyclin synthesis, modification and destruction in the control of cell division, *J. Cell Science*, Suppl. 12:77–97.

Misra, N. C. & Roberts, D. (1975), Inhibition by 4'-demethyl-epidophyllotoxin 9-(4,6-O-2-thenyldene-b-D-glycopyranoside) of human lymphoblast cultures in G2 phase of the cell cycle, *Cancer Research*, 35:99–105.

Mitchison, T. J., and Kirschner, M. W. 1984. Dynamic instability of microtubule growth. Nature 312:237–242.

Mitchison, T. J., and Kirschner, M. W. 1985. Properties of the kinetochore in vitro. II. Microtubule capture and ATP-dependent translocation. J. Cell Biol. 101:766–777.

Moore, E. C. (1969). Cancer Research 29, 291–295.

Morgan, D. O., et al. 1989. Mitosis-specific phosphorylation of p60$^{c\text{-}src}$ by p34$^{cdc2}$-associated protein kinase. Cell 57:775–786.

Mulner-Lorillon, O., et al. 1990. M-phase specific cdc2 protein kinase phosphorylates the beta subunit of casein kinase II and increases casein kinase II activity. Eur. J. Biochem. 193:529–534.

Murphy, P. 1976. The Neutrophil. Plenum Publishing Co., New York. 127 pp.

Murray, A. W., and Kirschner, M. W. (1989), Dominoes and clocks: the union of two views of the cell cycle, *Science*, 246:614–621.

Musk, S. R. R., et al. (1988), Caffeine induces uncoordinated expression of cell cycle functions after ultraviolet irradiation, *J. Cell Science*, 90:591–599.

Neant, I., and Guerrier, P. 1988. Meiosis reinitiation in the mollusc *Patella vialgata*. Regulation of MPF, CSF and chromosome condensation activity by intracellular pH, protein synthesis and phosphorylation. Development 102:505–516.

Newport, J., and Spann, T., 1987. Disassembly of the nucleus in mitotic extracts: membrane vesicularization, lamin disassembly, and chromosome condensation are independent processes. Cell 48:219–230.

Nishimoto, T., et al. (1978), Premature chromosome condensation in a ts DNA-Mutant of BHK Cells, *Cell*, 15:475–483.

Nurse, P. (1990), Universal control mechanism regulating onset of M-phase, *Nature*, 344:503–508.

O'Dwyer, P. J., et al. (1984), Teniposide: a review of 12 years of experience, *Cancer Treatment Reports*, 12:1455–1466.

Ohtsubo, M., et al. (1987), Isolation and characterization of the active cDNA of the human cell cycle gene (RCC1) involved in the regulation of onset of chromosome condensation, *Genes and Development*, 1:585–593.

Osmani, S. A., et al. (1988), Spindle formation and condensation in cells blocked at interphase by mutation of a negative cell cycle control gene, *Cell*, 52:241–251.

Paschal, B. M., et al. 1987. MAP1C is a microtubule-activated ATPase which translocates microtubules in vitro and has dynein-like properties. J. Cell Biol. 105:1273–1282.

Pelech, S. L., et al. 1988. Activation of myelin basic protein kinases during echinoderm oocyte maturation and egg fertilization. Dev. Biol. 130:28–36.

Peter, M., et al. 1990a. Identification of major nucleolar proteins as candidate mitotic substrates of cdc2 kinase. Cell 60:791–801.

Peter, M., et al. 1990b. In vitro disassembly of the nuclear lamina and M-phase-specific phosphorylation of lamins by cdc2 kinase. Cell 61:591–602.

Pfarr, C. M., et al. 1990. Cytoplasmic dynein is localized to kinetochores during mitosis. Nature 345:263–265.

Reed, S. I. (1991), G1-specific cyclins: in search of an S-phase promoting factor, *Trends in Genetics*, 7:95–99.

Riabowol, K., et al. 1989. The cdc2 kinase is a nuclear protein that is essential for mitosis in mammalian cells. Cell 57:393–401.

Rieder, C. L. & Alexander, S. P. (1990), Kinetochores are transported poleward along a single astral microtubule during chromosome attachment to the spindle in newt lung cells, *J. Cell Biology*, 110:81–95.

Rime, H., et al. 1989. 6-dimethylaminopurine (6-DMAP), a reversible inhibitor of the transition to metaphase during the first cell division of the mouse oocyte. Dev. Biol. 133:169–179.

Rober, R.-A., et al. 1990. Cells of the cellular immune and hematopoietic system of the mouse lack lamins A/C: distinction versus other cells. J. Cell Sci. 95:587–598.

Roberge, M., et al. (1990), The topoisomerase II inhibitor VM-26 induces marked changes in histone H1 kinase activity, histones H1 and H3 phosphorylation, and chromosome condensation in G2 phase and mitotic BHK cells, *J. Cell Biology*, 111:1753–1762.

Rowinsky, E. K., et al. (1990), Taxol: a novel investigational antimicrotubule agent, *J. Natl. Cancer Instit.*, 82:1247–1259.

Sawin, K. E., and Mitchison, T. J. 1991. Mitotic spindle assembly by two different paths in vitro. J. Cell Biol. 112:925–940.

Schaff, D. A., Jarrett, R. A., Dlouhy, S. R., Ponniah, S., Stockelman, M., Stambrook, P. J. and Tischfield, J. A. 1990. Mouse transgenes in human cells detect specific base substitutions. Proc. Natl. Acad. Sci. 87:8675–8679.

Schiff, P. B. & Horwitz, S. B. (1980). Proc. Natl. Acad. Sci. U.S.A. 77, 1561–1565.

Schlegel, R. & Pardee, A. B. (1986), Caffeine-induced uncoupling of mitosis from the completion of DNA replication in mammalian cells, *Science*, 232:1264–1266.

Schlegel, R., et al. (1990), Premature mitosis induced in mammalian cells by the protein kinase inhibitors 2-aminopurine and 6-dimethylaminopurine, *Cell Growth and Differentiation*, 1:171–178.

Shenoy, S., et al. 1989. Purified maturation promoting factor phosphorylates pp60$^{c\text{-}src}$ at the sites phosphorylated during fibroblast mitosis. Cell 57:763–774.

Speit, G., et al. 1990. Genetic effects of 2-aminopurine in mammalian cells. Mutagenesis 5:185–190.

Steinmann, K. E., et al. (1991), *roc. Natl. Acad. Sci. U.S.A.*, 88:6843–6847.

Steuer, E. R., et al. (1990), Localization of cytoplasmic dynein to mitotic spindles and kinetochores. Nature 345:266–268.

Takasaki, Y., et al. (1981), *J. Experimental Medicine*, 154:1899–1909.

Tate, E. H., et al. (1983) *Cytometry*, 4:211–215.

Tobey, R. A. 1973. Production and characterization of mammalian cells reversibly arrested in $G_1$ by growth in isoleucine-deficient medium. Meth. Cell. Biol. 6:67–112.

Vandre, D. D., et al. 1984. Phosphoproteins are components of mitotic microtubule organizing centers. Proc. Natl. Acad. Sci. USA 81:4439–4443.

Vandre, D. D., and Borisy, G. G. 1989. Anaphase onset and dephosphorylation of mitotic phosphoproteins occur concomitantly. J. Cell Sci. 94:245–258.

Verde, F., et al. 1990. Regulation of microtubule dynamics by cdc2 protein kinase in cell-free extracts of Xenopus eggs. Nature 343:233–238.

Weinert, T. A. & Hartwell, L. H. (1988), The RAD9 gene controls the cell cycle response to DNA damage in Saccharomycese cerevisiae, *Science*, 241:317–322.

Wood, E. R. & Earnshaw, W. C. (1990), J. Cell Biology 111, 2839–2850.

Yamashiro, S., et al. 1991. Phosphorylation of non-muscle caldesmon by p34$^{cdc2}$ kinase during mitosis. Nature 349:169–172.

Yamashita, K., et al, (1990), EMBO J., 9:4331–4338.

Zieve, G. W., et al. 1980. Production of large numbers of mitotic mammalian cells by use of the reversible microtubule inhibitor nocodazole. Exp. Cell Res. 126:397–404.

The embodiments of the invention in which an exclusive property or privilege is claimed are defined as follows:

1. A method of screening for a binary tumor therapy agent, comprising the steps:

contacting a cycling mammalian cell with a first agent that blocks progression of the cell cycle in the cell, wherein the first agent is selected form among agents that block the progression of the $G_1$, S, $G_2$, and mitosis stages of the cell cycle;

thereafter contacting the cell with a candidate second agent, wherein the candidate second agent comprises a purine ring system; and determining that the candidate second agent is a binary tumor therapy agent if the candidate second agent overrides the cell block such that the cell proceeds past mitosis and cell death results within an additional cell cycle due to aberrant DNA replication or chromosome segregation.

2. The method of claim 1, wherein the first agent blocks the mitosis stage of the cell cycle.

3. The method of claim 1, wherein the candidate second agent inhibits protein kinase activity.

* * * * *

UNITED STATES PATENT AND TRADEMARK OFFICE
CERTIFICATE OF CORRECTION

PATENT NO. : 5,262,409
DATED : November 16, 1993
INVENTOR(S) : R. L. Margolis et al.

It is certified that error appears in the above-indentified patent and that said Letters Patent is hereby corrected as shown below:

COLUMN        LINE
Title page item:

| | | |
|---|---|---|
| [75] "Inventors" | 2 | "Paul R. Andreasson" should read --Paul R. Andreassen-- |
| [56] "Other Publications" | 1st Publn. | "Bailel, E., et al." should read --Bailly, E. et al.-- |
| [56] "Other Publications" | 31st Publn. | "Weel$^{30}$-like" should read --Weel$^{+}$-like-- |
| [56] "Other Publications" | 39th Publn. | "Lungren, K., et al." should read --Lundgren, K., et al.-- |
| [56] "Other Publications" | 51st Publn. | "Kirscher, M. W." should read --Kirschner, M. W.-- |
| [56] "Other Publications" | 8th Publn. | "345:266-269" should read --345:266-268-- |
| [56] "Other Publications" | 90th Publn. | "mitsos" should read --mitosis-- |
| [56] "Other Publications" | 92th Publn. | after reversible insert --microtubule-- |
| 7 | 23 | "sceleroderma" should read --scleroderma-- |
| 7 | 35 | "other wise" should read --otherwise-- |

UNITED STATES PATENT AND TRADEMARK OFFICE
CERTIFICATE OF CORRECTION

PATENT NO. : 5,262,409

DATED : November 16, 1993

INVENTOR(S) : R. L. Margolis et al.

It is certified that error appears in the above-identified patent and that said Letters Patent is hereby corrected as shown below:

| COLUMN | LINE | |
|---|---|---|
| 16 | 38 | "aggrepate" should read --aggregate-- |
| 30 (Claim 1 | 13 Line 2) | "agent,comprising" should read --agent, comprising-- |
| 30 (Claim 1 | 16 Line 5) | "form" should read --from-- |

Signed and Sealed this

Twenty-eighth Day of June, 1994

Attest:

BRUCE LEHMAN

*Attesting Officer*          *Commissioner of Patents and Trademarks*